United States Patent
Hart et al.

[19]

[11] Patent Number: 6,162,196
[45] Date of Patent: Dec. 19, 2000

[54] MULTIPORT ACCESS DEVICE

[75] Inventors: Charles C. Hart, Huntington Beach; Nabil Hilal, Laguna Niguel, both of Calif.

[73] Assignee: Applied Medical Resources Corporation, Rancho Santa Margarita, Calif.

[21] Appl. No.: 09/191,759

[22] Filed: Nov. 12, 1998

Related U.S. Application Data

[63] Continuation-in-part of application No. 08/793,494, Jan. 14, 1996, which is a continuation-in-part of application No. 08/275,620, Jul. 14, 1994, Pat. No. 5,569,205.

[51] Int. Cl.[7] .................................................. A61M 5/00
[52] U.S. Cl. ............................................ 604/167; 604/256
[58] Field of Search .................................. 604/164, 165, 604/167, 168, 169, 256

[56] References Cited

U.S. PATENT DOCUMENTS

| | | | |
|---|---|---|---|
| 3,994,287 | 11/1976 | Turp et al. . | |
| 4,112,932 | 9/1978 | Chiulli . | |
| 4,180,068 | 12/1979 | Jacobsen et al. . | |
| 4,379,458 | 4/1983 | Bauer et al. .......................... | 604/264 |
| 4,601,710 | 7/1986 | Moll ...................................... | 604/165 |
| 4,654,030 | 3/1987 | Moll et al. ............................. | 604/165 |
| 4,869,717 | 9/1989 | Adair ..................................... | 604/51 |
| 4,929,235 | 5/1990 | Merry et al. .......................... | 604/167 |
| 4,931,042 | 6/1990 | Holmes et al. ....................... | 604/164 |
| 5,066,288 | 11/1991 | Deniega et al. ...................... | 604/274 |
| 5,116,353 | 5/1992 | Green .................................... | 606/184 |
| 5,197,955 | 3/1993 | Stephens et al. ..................... | 604/167 |
| 5,211,633 | 5/1993 | Stouder, Jr. ........................... | 604/167 |
| 5,269,763 | 12/1993 | Boehmer et al. .................... | 604/167 |
| 5,273,545 | 12/1993 | Hunt et al. ............................ | 604/167 |
| 5,300,036 | 4/1994 | Mueller et al. ....................... | 604/167 |

FOREIGN PATENT DOCUMENTS 0 479 130 A1   9/1991   European Pat. Off. .

*Primary Examiner*—John G. Weiss
*Assistant Examiner*—David J. Cho
*Attorney, Agent, or Firm*—Richard L. Myers, Esq.

[57] ABSTRACT

A trocar having a cannula and a valve housing with a polygonal configuration, provides for a floating septum where the float is encouraged in a first direction and restricted in a second direction. The septum includes multiple septum valves which may function with a common zero-closure valve, or individually in a valve assembly with an associated zero-closure valve. Various seals can be configured to prevent blow-back. Cup valves, check valves, and reciprocating valves are contemplated, along with various skirt configurations for maintaining pressurized air within the trocar.

39 Claims, 17 Drawing Sheets

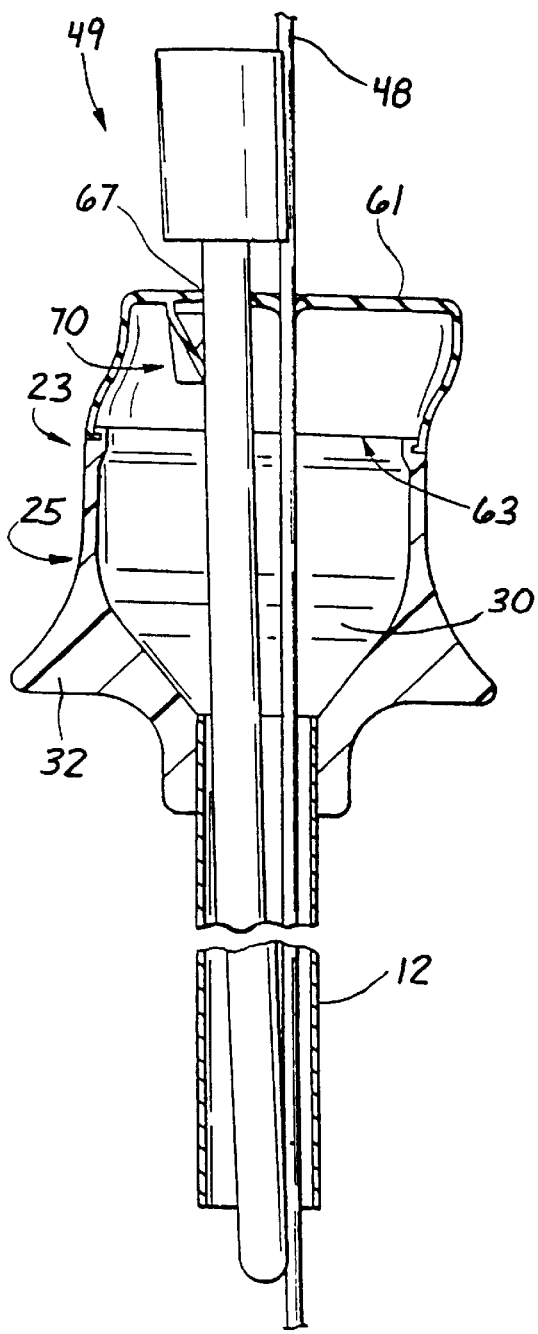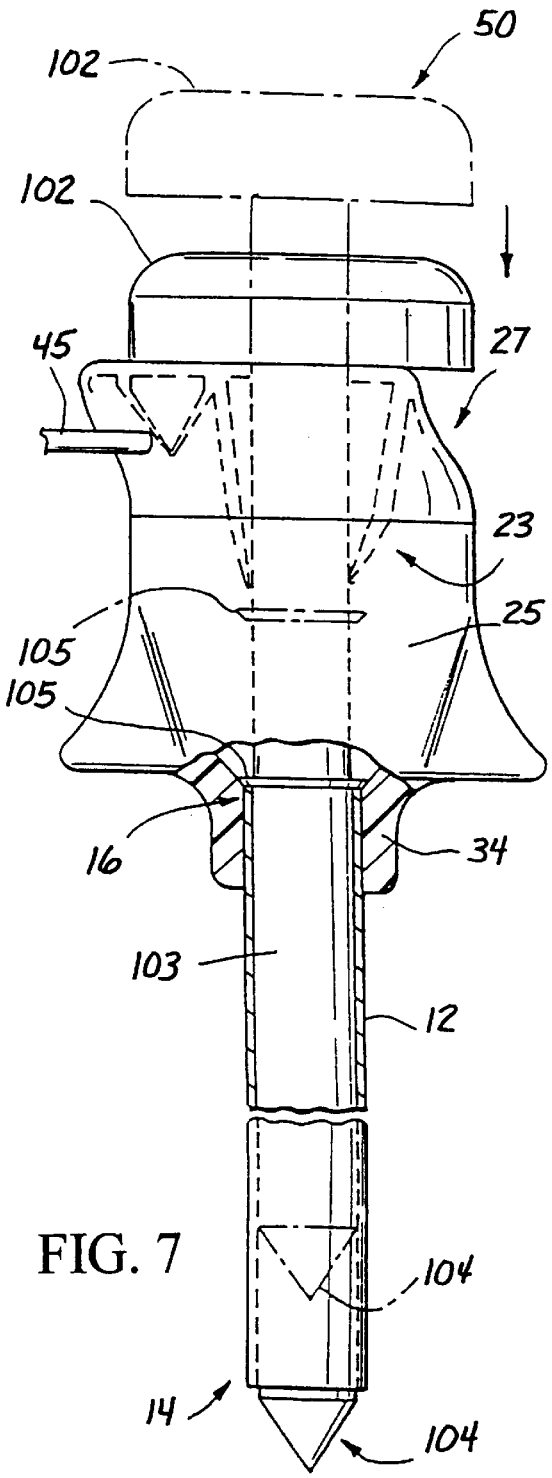
FIG. 6
FIG. 7

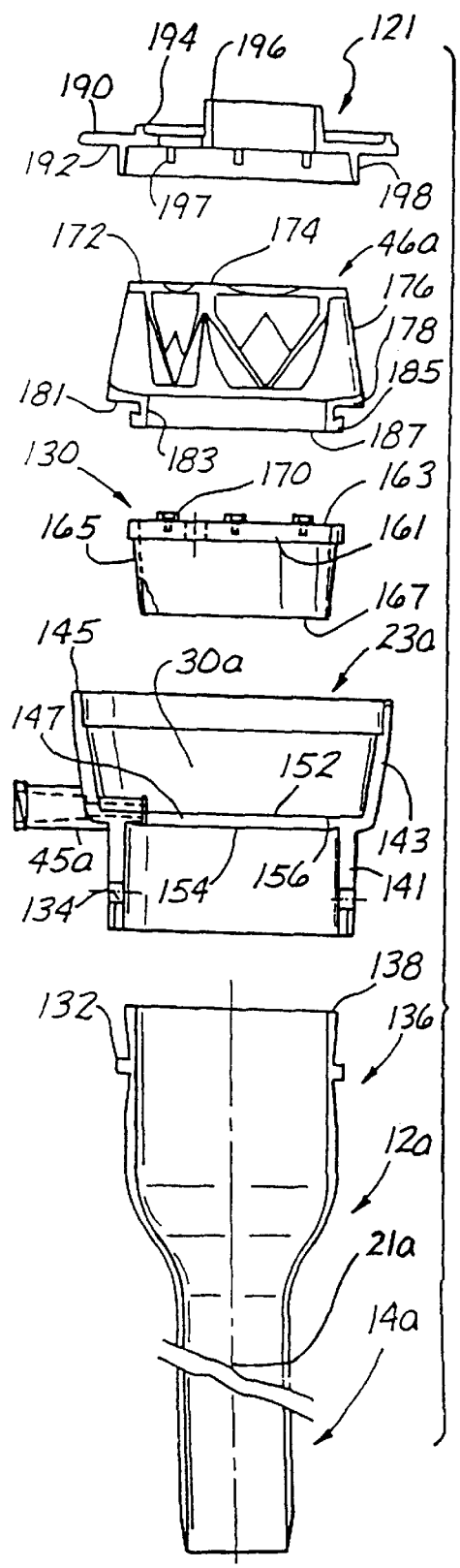
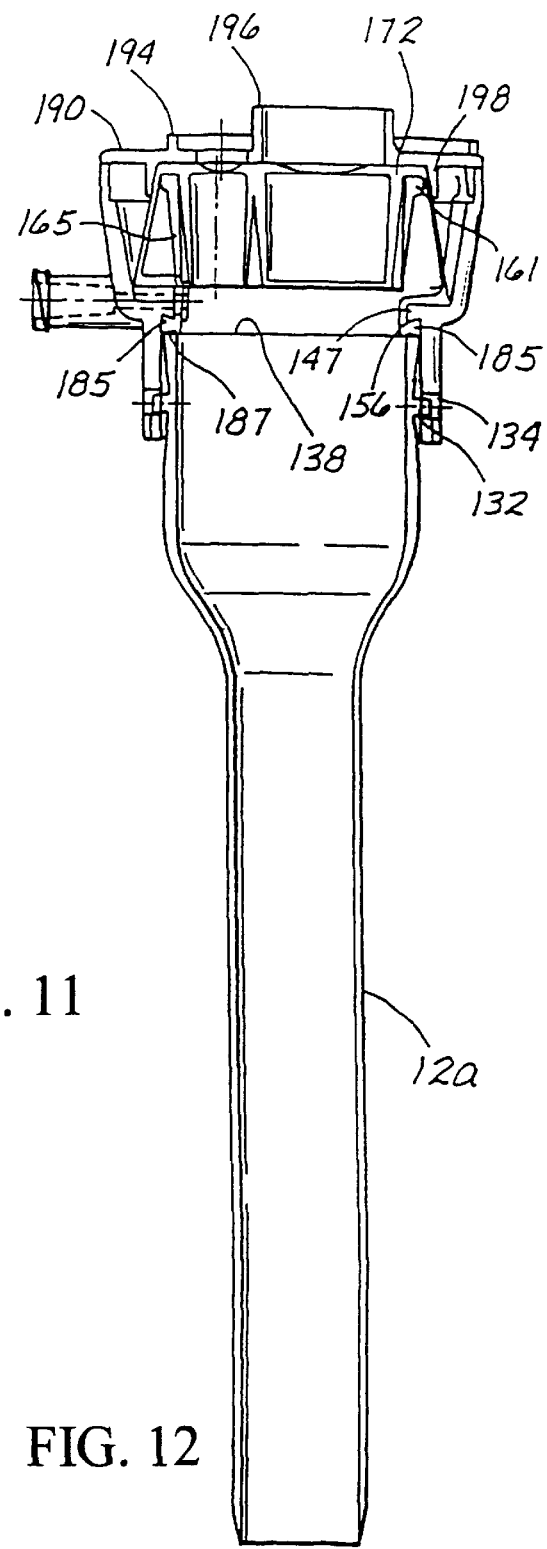
FIG. 11
FIG. 12

MULTIPORT ACCESS DEVICE

CROSS-REFERENCE TO RELATED APPLICATIONS

This application is a continuation-in-part of U.S. patent application Ser. No. 08/793,494, filed on Jan. 14, 1996, which is a continuation-in-part of U.S. patent application Ser. No. 08/275,620, filed on Jul. 14, 1994, and issued as U.S. Pat. No. 5,569,205 on Oct. 29, 1996, which are incorporated herein by reference.

BACKGROUND OF THE INVENTION

1. Field of the Invention

This invention relates generally to surgical access devices, such as trocars, which are adapted to provide access across a body wall and into a body conduit or cavity.

2. Discussion of the Prior Art

Trocars of the past have typically included a cannula and a valve housing which together define an access or working channel for various surgical instruments. The cannula has been fonned in the configuration of an elongate rigid cylinder which has been inserted, with the help of an obturator, into a body cavity, such as the abdominal cavity to provide access across a body wall, such as the abdominal wall.

In a typical abdominal laparoscopic surgery, the abdomen is insufflated to pressurize and thereby enlarge the cavity within which a surgical procedure is to be performed. Various instruments used in the procedure have been inserted, previously one at a time, through the working channel of the trocar to perform the surgery. Ill order to maintain the insufflation pressure when the instrument is inserted through the trocar, a valve has been provided in the housing to form a seal around the instrument. These instrument valves have typically been provided in the form of septum valves. When the instrument is removed, a zero-closure valve has typically been provided to seal the trocar in order to maintain the insufflation pressure.

A septum valve similar to that disclosed and claimed by applicant in copending application Ser. No. 08/051,609 filed Apr. 23, 1993 and entitled Seal Assembly for Access Device is typical of the instrument valves. A typical zero-closure valve might be in the form of a double duck bill valve such as that disclosed in the same application which is incorporated herein by reference.

Instruments vary in size and diameter. While the zero-closure valves of the past can accommodate a relatively wide range of diameters, the septum valves are generally capable of stretching only a nominal amount to accommodate larger diameters. Accordingly, these valve sets are generally limited as to the size of instrument which they can accommodate. Attempts have been made to increase the range of septum valves by providing levers which prestretch the valve in order to reduce some of the friction forces. These universal septum valves, such as those disclosed and claimed by applicant in U.S. Pat. No. 5,209,737, are relatively complex in structure but nevertheless are able to accommodate a wide range of instruments.

In trocars of the past, the septum valves and zero-closure valves have been formed as a valve set. This set has typically been configured along a common axis which extends through the opening of the septum valve, the zero-closure valve, and the cannula.

In the past, only a single valve set was provided in the trocar. This necessitated that instruments used with the trocar be inserted only one at a time. Thus a first instrument would be inserted through the septum valve and the zero-closure valve to gain access to the abdominal cavity. With the instrument in place, the septum valve would maintain the insufflation pressure. Once the first instrument was removed, this insufflation pressure was maintained by the zero-closure valve. Only upon removal of the first instrument could a second instrument be inserted through the same septum valve and the same zero-closure valve.

When an instrument was required that had a diameter outside the range of a particular valve set, the entire trocar had to be replaced with one which could accommodate a different range of diameters. In some cases alternative septum valves were provided each of which functioned with the same zero-closure valve but accommodated a different range of instrument diameters. Even where the trocars of the past provided for alternative valve sets, only a single instrument could be inserted at a time.

SUMMARY OF THE INVENTION

These deficiencies of the prior art have been overcome with the present invention which provides for the insertion of two or more instruments into the same trocar at the same time. This trocar which provides for a seal assembly having multiple valve sets in a single valve housing, is significantly simplified so that manufacturing costs are greatly reduced.

Each of the valve sets in a preferred embodiment accommodates a different range of instrument sizes so that only a single trocar and seal assembly is required in order to accommodate all possible instrument sizes. Thus, a single simplified trocar can accommodate not only a full range of instrument sizes, but can even accommodate multiple instruments simultaneously. Not only is the single trocar less expensive to manufacture, but the number of assemblies and trocars required for a given surgical operation is also reduced. This will be greatly appreciated in a cost sensitive marketplace where as many as one million laparoscopic surgeries are performed annually in the United States, each requiring as many as four to six trocars per surgery.

Each of the valve sets is provided with characteristics for forming an instrument seal as well as a zero-closure seal. These characteristics can be provided for the smallest range of instruments, by a single septum valve which additionally has zero-closure characteristics. For larger valve sets, a septum valve is combined with a zero-closure valve in each of the sets. In an embodiment wherein the cannula has a first axis, the septum valve a second axis, and the zero-closure valve a third axis, at least one of the second and third axes is offset from the first axis. It may also be desirable to offset the second axis of the second septum valve from the third axis of the zero-closure valve in order to accommodate more valve sets in the single valve housing. In these embodiments, the zero-closure valves can be formed in any manner associated with the prior art, but the double duck bill valve configuration is preferred.

In one aspect of the invention, a trocar is adapted to extend across a body wall into a body cavity, and to form a seal around an instrument inserted through the trocar into the body cavity. The trocar comprises a cannula forming an elongate passage and a valve housing disposed at a proximal end of the trocar. A valve assembly is disposed relative to the housing and includes a first valve set forming a first working channel with the passage of the cannula and a second valve set forming a second working channel with the passage of the cannula. The first valve set includes a first septum valve and a first zero-closure valve each disposed along the first working channel. The second valve set includes a second septum valve and second zero-closure valve each disposed along the second working channel. The trocar further comprises means for further supporting at least one of the first septum valve and the second septum valve relative to the housing in a "floating" relationship with the cannula.

In an additional aspect of the invention, a trocar assembly includes a cannula having an axis extending between a proximal end and a distal end. A housing disposed at the distal end of the cannula includes a rigid housing portion fixed to the cannula and an axially compressible elastomeric housing portion disposed proximally of the rigid housing portion. Together the rigid and elastomeric housing portions form a working channel with the cannula of the trocar. This channel is sized and configured to receive an obturator having a shaft with an axis extending to a sharp distal tip. When the obturator is operatively disposed, this distal tip extends beyond the distal end of the cannula. The trocar assembly includes means associated with the shaft of the obturator and at least one of the cannula and the rigid housing portion for preventing insertion of the obturator into the cannula beyond the operative position of the obturator in order to avoid substantial axial compression of the elastomeric housing portion.

In a further aspect of the invention, a trocar assembly includes a cannula having a first axis and a valve housing forming a working channel with the cannula. A first septum valve is disposed relative to the housing and includes portions defining a first opening having a second axis. A second septum valve is disposed relative to the housing and has portions defining a second opening having a third axis. At least one of the second axis of the first septum valve and the third axis of the second septum valve is offset from the first axis of the cannula.

In still a further aspect of the invention, a trocar includes a cannula having a first axis and a septum valve disposed along the working channel of the trocar and forming an opening having a second axis. The septum valve is formed of an elastomeric material stretchable between a first natural position wherein the opening of the septum valve is disposed with the second axis offset from the first axis of the cannula, and a second stretched position wherein the second axis of the septum valve is generally aligned with the first axis of the cannula. Means is provided for supporting the septum valve relative to the cannula to permit movement of the septum valve from the first natural position to the second stretched position without substantial deformation of the opening of the septum valve.

Other aspects of the invention provide structural accommodation for various embodiments of a valve assembly including more than one valve set. In one case, the valve assembly includes an elastomeric sidewall that connects proximal portions of the valve assembly with distal portions of the valve assembly. The distal portions are sandwiched between the cannula and valve housing to form a seal with these elements. The valve housing extends to a proximal wall where the proximal portions of the valve assembly engage an end cap which is movable transverse of the trocar axis in contact with the proximal surface of the valve housing. The sidewall of the valve assembly is held in elastomeric tension to bias the end cap against the valve housing.

Transverse movement of the end cap is limited by a projection which extends from either the valve housing or the end cap to provide an interference fit between the projection and the other of the valve housing and end cap.

A rigid partition is provided within the valve housing and extends along the axial length of the valve sets. This rigid partition is movable with the end cap and the valve assembly to inhibit contact between the sidewalls of the housing and the axial walls of the valves which would otherwise undesirably deform the valves and permit leakage of the insufflation gas.

Another aspect of the invention provides for a valve housing having the configuration of a polygon in radial cross-section. This housing accommodates a floating septum with movement facilitated in one direction while movement is inhibited in a second, transverse direction. Multiple septum valves can function with a common zero-closure valve or can each be provided with an associated zero-closure valve. Blow-back, which may be a problem in the first instance, can be inhibited with check valves and reciprocating valves, which operate independently or in combination to alternatively block the non-operative septum valve. Various skirt configurations can also be employed to maintain air pressure within the trocar.

These and other features and advantages of the invention will become more apparent with the description of preferred embodiments and reference to the associated drawings.

DESCRIPTION OF THE DRAWINGS

FIG. 6 is a cross-section view similar to FIG. 2 and illustrating a small sized instrument and a medium sized instrument simultaneously operatively disposed through first and second valve sets of the trocar;

FIG. 7 is a radial cross-section view similar to FIG. 6 and illustrating a large instrument in the form of an obturator operatively disposed in the trocar;

FIG. 11 is an exploded axial cross-section view of the trocar embodiment of FIG. 10 illustrating components including (from top to bottom) an end cap, a valve assembly, a partition structure, a valve housing, and a cannula;

FIG. 12 is an axial cross-section assembled view of the trocar illustrated in FIG. 11;

DESCRIPTION OF PREFERRED EMBODIMENTS

Figure 1:
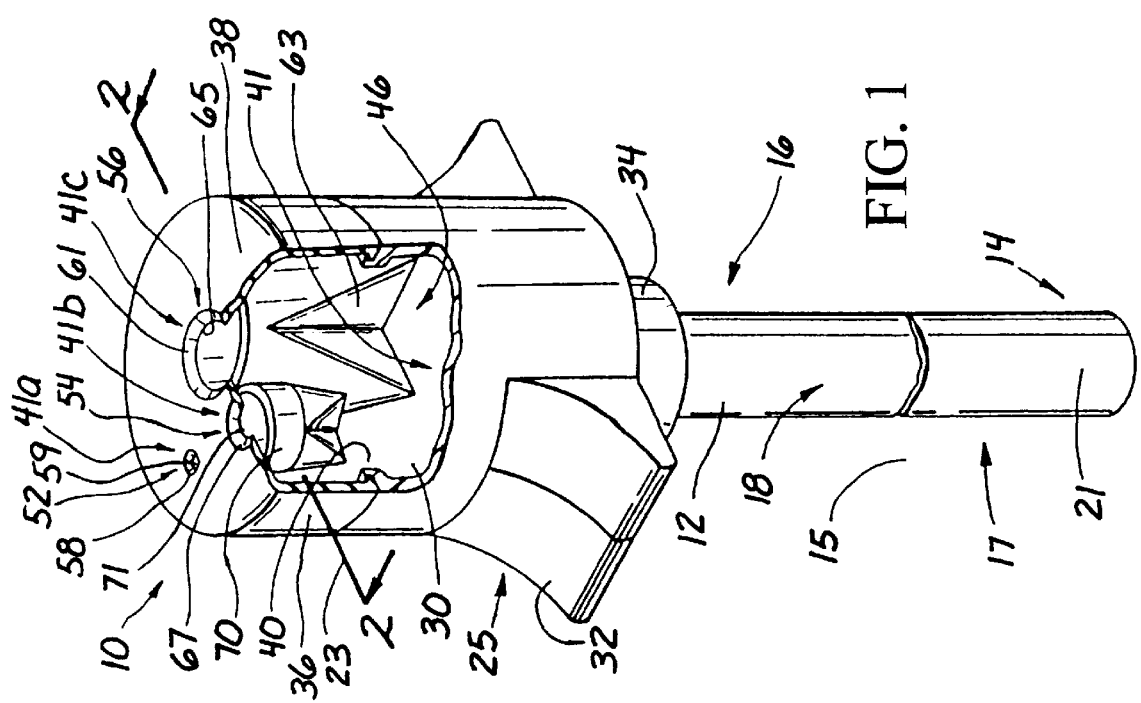
FIG. 1 is a perspective view of a preferred embodiment of the trocar of the present invention.

A multiport trocar is illustrated in FIG. 1 and designated generally by the reference numeral 10. The trocar 10 is representative of any access device including a cannula 12 which is in the form of a hollow elongate cylinder having a distal end 14 and a proximal end 16. It is this cannula 12 which is sized and configured to extend across a body wall, such as an abdominal wall 15, into a body conduit or cavity, such as a blood vessel or an abdominal cavity 17. The cannula 12 is preferably rigid, or semi-rigid and in preferred embodiments is formed of plastics or surgically compatible metals such as stainless steel. A passage 18 formed by the walls of the cannula 12 extends along a central axis 21.

A valve housing 23 also forms a significant part of the trocar 10. In the illustrated embodiment, the valve housing 23 includes a rigid housing portion 25 and an elastomeric housing portion 27 which together define a housing cavity 30.

Figure 2:
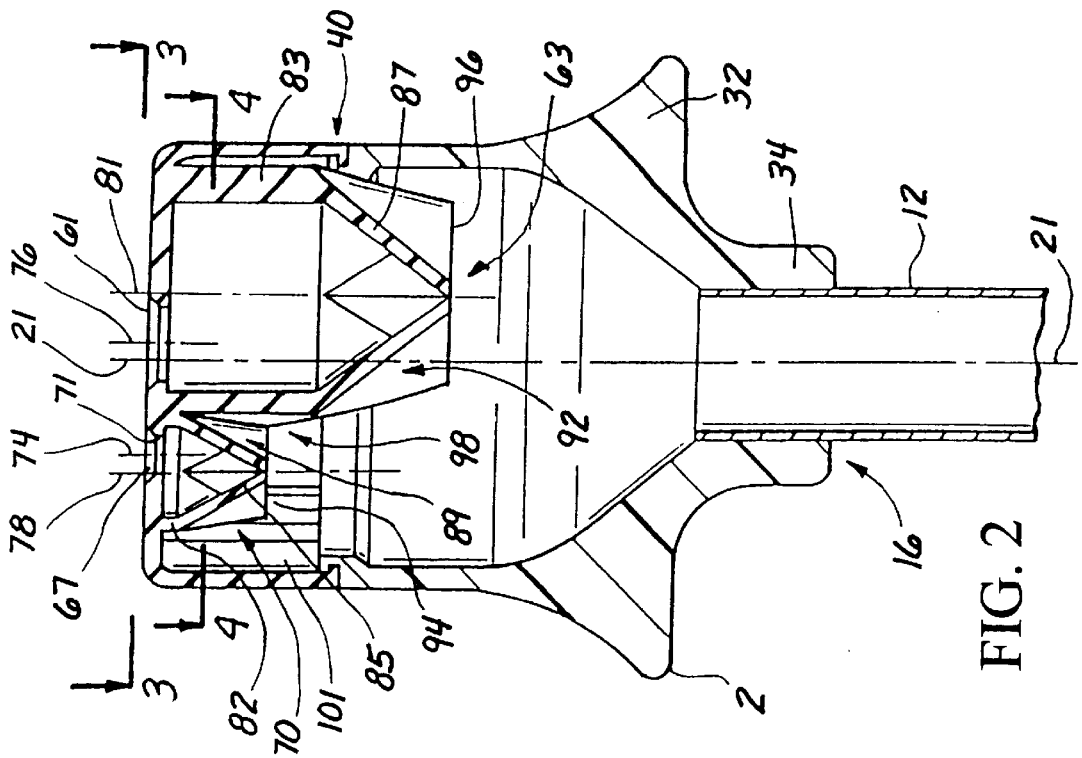
FIG. 2 is an axial cross-section view taken along lines 2—2 of FIG. 1, and illustrating a preferred embodiment of a valve housing and associated valve assembly.

The rigid housing portion 25 is preferably formed of plastic and disposed at the proximal end 16 in a fixed relationship with the cannula 12. In the illustrated embodiment, a pair of finger tabs 32 are formed as an integral part of the rigid housing portion 25 and provide means for engaging the trocar 10 and manipulating the cannula 12 into a preferred operative position. A collar 34 is disposed distally of the tabs 32 where it is sized and configured to receive the proximal end 16 of the cannula 12, as best illustrated in FIG. 2.

The elastomeric housing portion 27 is preferably formed from a resilient material, and includes a cylindrical side wall 36 and an end wall 38 that are integral in a preferred embodiment. A resilient material may include natural rubber or, preferably, a non-rubber material such as nitrile, silicone, or a urethane. The side wall 36 is preferably centered on the axis 21 of the cannula 12 while the end wall 38 is transverse, for example perpendicular, to the axis 21. In a preferred embodiment, the side wall 36 of the elastomeric housing portion 27 is joined to and forms a seal with the rigid housing portion 25 at a circumferential joint 40.

The cavity 30 formed by the valve housing 23 is in fluid communication with the passage 18 of the cannula 12. Together this cavity 30 and passage 18 form a working channel 41 of the trocar 10. In the illustrated embodiment, this channel 41 extends from regions exterior of the trocar 10, through the end wall 38, into the housing cavity 30, and through the passage 18 and the distal end 14 of the cannula 12. Thus the trocar 10 functions as an access device so that instruments can be inserted through the seal housing 23 and the cannula 12 into the abdominal cavity 17.

In a typical laparoscopic surgery, the trocar 10 is disposed with the cannula 12 extending across the abdominal wall 15 and into the abdominal cavity 17. In order to increase the working space at the surgical site, the abdominal cavity 17 is typically pressurized or insufflated. In the trocar 10 illustrated in FIG. 3, this insufflation of the abdominal cavity 17 is implemented by use of an insufflation tube 45 which is in fluid communication with the housing cavity 30 as well as the passage 18 of the cannula 12.

After the abdominal cavity 17 is appropriately insufflated, various instruments, such as catheters, guide wires, graspers, staplers, can be inserted through the working channel 41 of the trocar 10 to perform various functions within the abdominal cavity 17. It is important in such an operation, that the insufflation pressure be maintained both when the instruments are disposed within the working channel 41 of the trocar 10, as well as when the instruments are removed from the working channel 41. Such is the function of a valve assembly 46 which is typically disposed within the housing cavity 30 or formed as part of the valve housing 23.

The valve assembly 46 of the present invention is sized and configured to accommodate a surgical instrument having substantially any diameter regardless of the size limitations of a single valve. Such instruments are represented by a catheter 48, a retractor 49 and a obturator 50 best illustrated in FIGS. 6 and 7. In the following discussion, the catheter 48, retractor 49 and obturator 50 are sometimes referred to respectively as the small, medium and large instruments 48, 49, 50, and collectively as the instruments 48, 49 and 50.

As noted, these instruments 48–50 will vary widely in diameter. For example, the small size instrument 48 might include a guidewire or catheter up to two millimeters in diameter. The medium size instrument 49 might include graspers or retractors between two and five millimeters in diameter. The large size instrument 50 might include an obturator or laparoscope having diameters as small as five millimeters and as large as eleven or twelve millimeters.

This entire range of diameters, for example from zero to eleven or twelve millimeters, can be accommodated with the single multiport trocar 10 of the present invention. In this concept, the valve assembly 46 includes at least two and preferably three or four valve sets each adapted to receive a different range of instrument sizes, and collectively to accommodate the entire range of instrument sizes. In the illustrated embodiment the valve assembly 46 includes a small valve set 52, a medium valve set 54 and a large valve set 56. These valve sets 52, 54 and 56 form, with the passage 18 of the cannula 12, three respective working channels 41a, 41b, and 41c.

Each of the valve sets 52–56 must have characteristics for forming a seal around the associated instrument 48–50 when it is operably disposed in the working channel 41, as well as characteristics for forming a seal across the working channel 41 when the associated instrument 48–50 is removed. For the small valve set 52, both of these characteristics can be provided by a single septum valve 58 which has an opening 59 small enough to close upon itself in the absence of the instrument 48, but large enough to accommodate instruments of up to about two millimeters in diameter.

The large valve set 56 is representative of the other valve sets in the valve assembly 46. This large valve set 56 includes a large septum valve 61 as well as a large zero-closure valve 63. These valves 61 and 63 can be of the type disclosed in applicant's copending application Ser. No. 08/051,609 filed on Apr. 23, 1993 and entitled "Seal Assembly for Access Device".

In order to accommodate a large instrument, such as the obturator 50, the large septum valve 61 is provided with a hole 65 which in its natural state has a diameter, such as about five millimeters. Forcing the instrument 50 with a diameter larger than about five millimeters through this hole 65 causes the valve 61 to expand so that it forms a tight seal with the outer surface of the instrument 50. However, when the instrument 50 is removed, the septum valve returns to its natural state leaving the hole 65 in an open state. Under these circumstances, the zero-closure valve 63 is of particular importance as it fully closes in the absence of the instrument 50. This insures that the working channel 41c through the large valve set 56 is fully closed when the instrument 50 is removed.

The medium valve set 54 is similar to the large valve set 56 in its function, however, it is generally smaller in size. Thus the medium valve set 54 includes a medium septum valve 67 and a medium zero-closure valve 70. As was the case with the large septum valve 61, the medium septum valve 67 has a hole 71 which is sufficiently large to accommodate medium size instruments between about two millimeters and five millimeters, for example. This medium septum valve 67 does not fully close as did the small septum valve 58, so the zero-closure valve 70 is required to seal the working channel 41b through the medium valve set 54 when the instrument 49 is removed.

Figure 3:
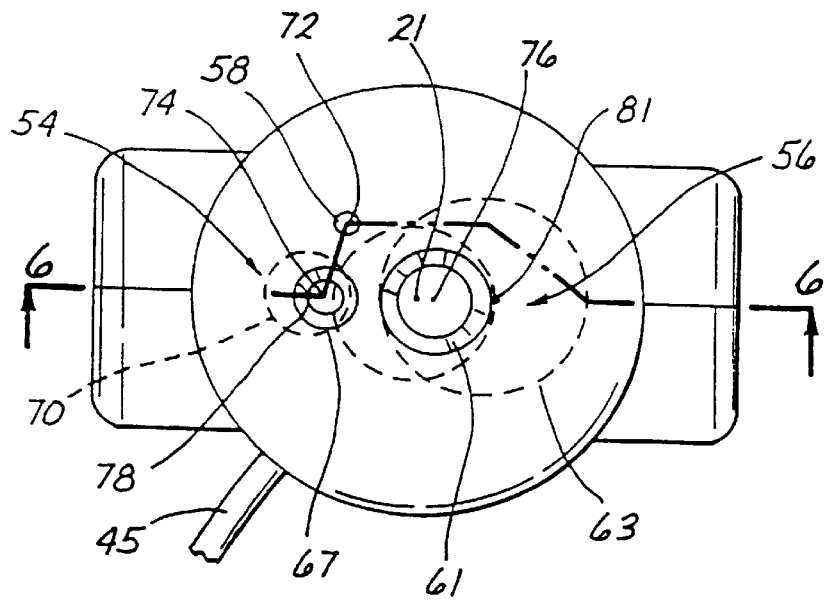
FIG. 3 is a top plan view taken along lines 3—3 of FIG. 2.

In order to accommodated the multiple valve sets 52–56 within a single valve housing 23, the lateral orientation of the respective septum valves 58, 67 and 61 in the end wall 38 can be of particular importance. With reference to FIG. 3, it will be noted that the three septum valves 58, 67 and 61 are each centered on an associated longitudinal axis 72, 74 and 76. Similarly, the zero-closure valves 70 and 63 are centered on respective longitudinal axes 78 and 81.

Each of the axes 72–76, associated with the respective septum valves 58, 67, and 61, is separated or off set from the axis 21 of the trocar 10 by a different distance. In the illustrated embodiment the axis 76 associated with the large septum 61 is disposed closest to the axis 21. This orientation is preferred since a larger instrument, such as the obturator 50, requires a more vertical orientation with the trocar 10 due to the fact that its diameter more closely approaches that of the cannula 12. Thus, by locating the axis 76 relatively close to the axis 21, the septum valve 61 is required to move only a small distance in order to achieve the more vertical orientation required by the large instrument 50.

As illustrated in FIG. 6, the medium sized instruments, such as the retractor 49, can pass through the cannula 12 at an angle so that the medium size instrument 49 does not require as vertical an orientation as the large instrument 50. Thus the medium septum valve 67 need not move as close to the axis 21 of the cannula 12 for operative disposition of the instrument 49. For this reason, the axis 74 of the medium septum valve 67 can be offset from the axis 21 of the cannula 12 a distance greater than that separating the axis 76 of the large septum valve 61 from the axis 21 of the cannula 12. With respect to the small septum 58, its axis 72 can be located at an even greater distance from the axis 21. Not only do small instruments, such as guidewires and the catheter 48, require very little vertical orientation, but they are often flexible so that no movement of the septum 58 is required for operative disposition of these small instruments.

For the reasons just discussed, it is important that the septum valves 61 and 67 be located so that they can move from their natural position, in the absence of the instruments 49, 50 to a more centered position, in the presence of the instruments 49, 50. This movement must occur without substantial deformation of the septum valve 67 and 61 so that the valve portions forming the respective holes 71 and 65 can form a suitable seal with the outer surface of the instruments 49, 50.

The movement of the septum valves 61 and 67 is referred to herein as flotation, which generally includes two types of movement. The first type of flotation is associated with valve selection, while the second type of flotation is associated with seal maintenance during instrument manipulation. More specifically, the first type of flotation associated with valve selection provides for movement of the valves 61 and 67 between a first position wherein the valve 61 is operatively disposed, and a second position wherein the valve 67 is operatively disposed. When either of these valves 61 and 67 is operatively disposed, instrument manipulation can give rise to a cat eye effect where proper seal formation is inhibited by movement of the instrument. Flotation of the valves 61 and 67 facilitate maintenance of the associated seals even during instrument manipulation. In a preferred embodiment, these two types of flotation are independent of each other.

In a preferred embodiment, this movement without deformation is accommodated by two characteristics of the trocar 10. First, the end wall 38 is formed of an elastomeric material thereby permitting the septum valves 58, 67 and 61 to move laterally within the end wall 38. Perhaps more importantly, the side wall 36 of the housing portion 27 is also formed of an elastomeric material and is easily deflected laterally. This movement of the side wall 36 carries the entire end wall 38 to a desired position without deformation of the associated septum valve 58, 67 and 61. Thus the septum valves 58, 67 and 61 have a floating relationship with the cannula 12 which permits them to move laterally while still maintaining their properties for forming a seal with the outer surface of the associated instrument 48–50. This lateral deflection of the side wall 36 is illustrated in both FIGS. 6 and 7 for the respective instruments 49 and 50.

In the foregoing embodiment, the septum valves 58, 67 and 61 are formed in the end wall 38 of the elastomeric housing portion 27. It will be apparent, however, that these valve 58, 67 and 61 can be formed generally in any wall which is transverse to the axis 21 of the cannula 12. The resulting valve wall can be included within the housing cavity 30 or can form part of the valve housing 23. Nevertheless, it is generally preferred that the septum valves 58, 67, and 61 be formed in the proximal-most wall, such as the end wall 38, of the valve housing 23.

The location of the zero-closure valve 70 and 63 can also be critical in a particular embodiment. It is not required that the axes 78 and 81 associated with the zero-closure valves 70 and 63 respectively, be aligned with the axes 74 and 76 of the associated septum valves 67 and 61. This alignment of valves within a valve set, which is characteristic of the prior art, is not required by the present invention. Rather the location of the zero-closure valves 70 and 63 is generally dependent on two different considerations.

First, the zero-closure valve 70 must be positioned such that the instrument 49 passing through the associated septum valve 67 also passes through a zero-closure valve 70. Similarly, the zero-closure valve 63 must be positioned so that the instrument 50, passing through the associated septum valve 61 also passes through the zero-closure valve 63. As can be seen from FIG. 3, this requirement is not particularly stringent so that the septum valves 67 and 61 can be located relatively close to the central axis 21 while the associated zero-closure valve 70 and 63 are located relatively far from the central axis 21.

The second consideration for location of the zero-closure valves 70 and 63, is based on their proximity to each other. It is important that when the medium instrument 49 is positioned within the medium valve set 54, that it not interfere with the ability of the large zero-closure valve 63 to seal the working channel 41c. This generally requires that the medium zero-closure valve 70 be separated from the large zero-closure valve 63 a distance sufficient to prevent deformation of the large zero-closure valve 63.

In the illustrated embodiment, this interference with a non-associated zero-closure valve 63 is of perhaps greatest concern with respect to the medium valve set 54. In this valve set 54, the medium instrument 49 will typically have a more angled disposition within the housing cavity 30 than the large instrument 50. Furthermore, the large zero-closure valve 63 will typically extend further into the housing cavity 30, as illustrated in FIG. 2, making it more susceptible to interference from the medium instrument 49.

Figure 4:
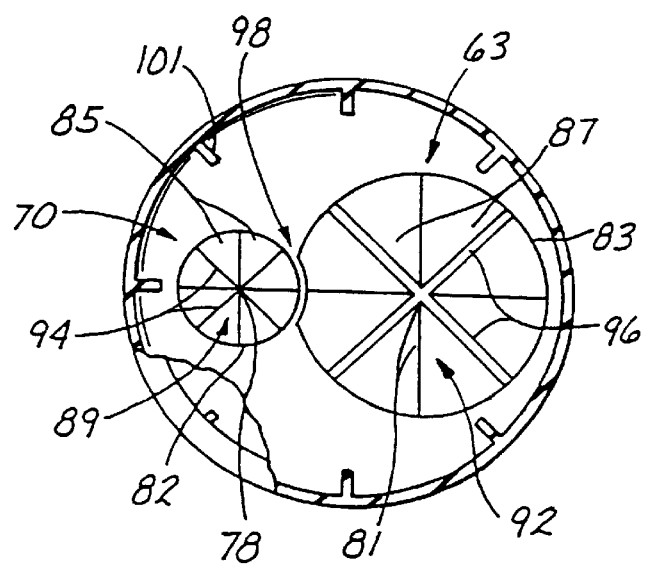
FIG. 4 is a radial cross-section view taken along lines 4—4 of FIG. 2.
Figure 5:
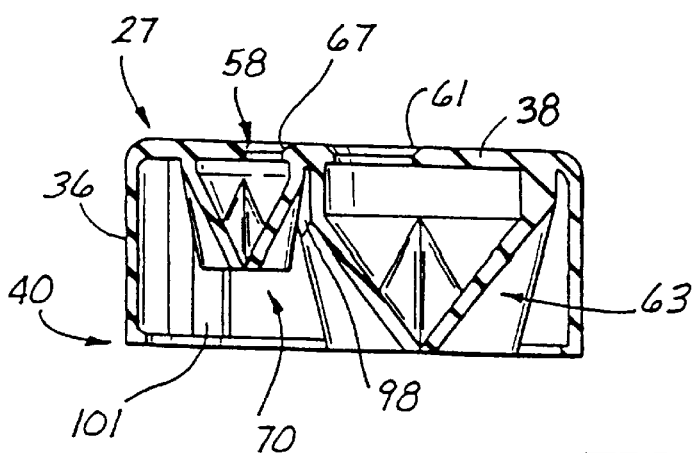
FIG. 5 is an axial cross-section view similar to FIG. 2 and illustrating an additional embodiment of a valve housing.

The double duck bill valve configuration illustrated for the zero-closure valves 63 and 70 is particularly beneficial in avoiding this interference. Each of these zero-closure valves 70 and 63 includes respectively, a cylindrical side wall 82 and 83, and a closure structure defined by walls 85 and 87. These walls 85, 87 define lateral recesses 89, 92 as they converge to lines 94, 96, respectively, which form the cross seal associated with this type of zero-closure valve. These lines 94 and 96 are best illustrated in FIG. 4. The configuration of the walls 85, 87 and the associated recesses 89, 92 and lines 94, 96 are described in greater detail in applicant's copending application Ser. No. 08/051,609.

In general, this configuration of the zero-closure valves 70 and 63 facilitates a structure wherein one of the valves, such as the valve 70, can be provided with a side wall, such as the side wall 82, which is shorter than the side wall, for example the side 83, associated with the other zero-closure valve, such as the valve 70. Then, a recess or indentation 98, can be formed in the other side wall, such as the side wall 83. It will be apparent that this solution will be equally appropriate with a longer side wall 82 in the medium zero-closure valve 70, and an appropriate indentation, such as the indentation 98, in that side wall 82.

Another way of accommodating the close proximity of the zero-closure valves 70 and 63 is to orient the associated seal lines 94 and 96 so that neither is disposed along a line interconnecting the axes 78 and 81 of the respective valve 70 and 63. Since these seal lines 94 and 96 extend to the greatest diameter of the associated walls 85 and 87 they are most susceptible to interference by an instrument extending through the opposite valve set 54, 56. By orienting these lines 94 and 96, as illustrated in FIG. 4, the natural recesses 89 and 92 formed between lines 94, 96 are automatically faced toward the opposing axis 78, 81.

As one contemplates an appropriate length for either of the side walls 82, 83, it must be appreciated that additional length will ultimately demand a longer valve housing 23. For comparison, it will be noted that in the embodiment of FIG. 2, the zero-closure valve 63 extends beyond the joint 40 between the rigid housing portion 25 and the elastomeric housing portion 27. In an embodiment wherein the length of the seal housing 23 is to be minimized, it may be desirable to shorten the side walls 83 associated with the zero-closure valve 63. This could produce an embodiment wherein neither of the zero-closure valves 63 or 70 extends beyond the joint 40 between the housing portions 25 and 27.

When an instrument, such as the instruments 49 and 50, is removed from the trocar 10, it is desirable that the elastomeric housing portion 27 return to its natural state wherein its side wall 36 is coaxial with the central axis 21. This return to the natural state is facilitated in a preferred embodiment wherein the housing portion 27 is provided with a plurality of ribs 101 which extend radially and longitudinally of the side wall 36 within the housing cavity 30.

In a preferred embodiment, the entire elastomeric housing portion 27 (including the ribs 101) and the entire valve assembly 46 (including the septum valves 58, 67, 61 and the zero-closure valves 70, 63) are formed as an integral structure from an elastomeric or resilient material such as latex.

The lateral flexibility desired for the elastomeric housing portion 27 also produces an axial flexibility which may not be desired when the trocar 10 is used with obturators of the prior art. As illustrated in FIG. 7, the obturator 50 of the present invention is typical of those of the past in that it includes a handle 102 and a shaft 103 having a sharp distal tip 104. This obturator 50 is designed for axial insertion through the valve housing 23 and into the cannula 12 as illustrated by the dotted line position in FIG. 7. Further axial movement into the cannula 12 brings the obturator 50 to an operative position where the sharp distal tip 104 of the obturator 50 extends beyond the distal end 14 of the cannula 12. This operative position is shown by the solid line position of the obturator 50 in FIG. 7. Once the obturator 50 is disposed in its operative position within the cannula 12, further axial pressure on the handle 102 is intended to force the sharp distal tip 104 through the abdominal wall 15 to position the distal end 14 of the cannula 12 within the abdominal cavity 14.

With obturators of the past, this axial pressure was directed through the handle and applied against the proximal end of the valve housing. In the present invention, however, this additional pressure on the proximal end of the housing 23 would only seek to compress the elastomeric housing portion 27. This would not only make it difficult to insure the operative disposition of the sharp tip 104 beyond the cannula 12, but also could damage the elastomeric housing portion 27.

In a preferred embodiment, illustrated in FIG. 7, the obturator 50 is provided with an enlargement or projection 105 which is fixed to the outer surface of the shaft 95. In the illustrated embodiment, the projection 105 takes the form of an annular flange which extends radially outwardly from the outer surface of the shaft 103. When the obturator 50 is inserted from its dotted line position in FIG. 7 to its solid line operative position, this projection 105 moves through the housing cavity 30 into engagement with the proximal end 16 of the cannula 12 which finctions as a stop for the projection 105. Since the projection 105 is larger than the inside diameter of the cannula 12 in this embodiment, further axial movement of the obturator 50 is prevented. In this operative position of the obturator 50, the distal tip 104 of the shaft 103 extends beyond the distal end 14 of the cannula 12, but the handle 102 does not axially compress the elastomeric housing portion 27. In general, the projection 105 can be positioned along the shaft 102 at any location where it can engage part of the rigid housing portion 25, such as the collar 34, or the proximal end 16 of the cannula 12.

Figure 10:
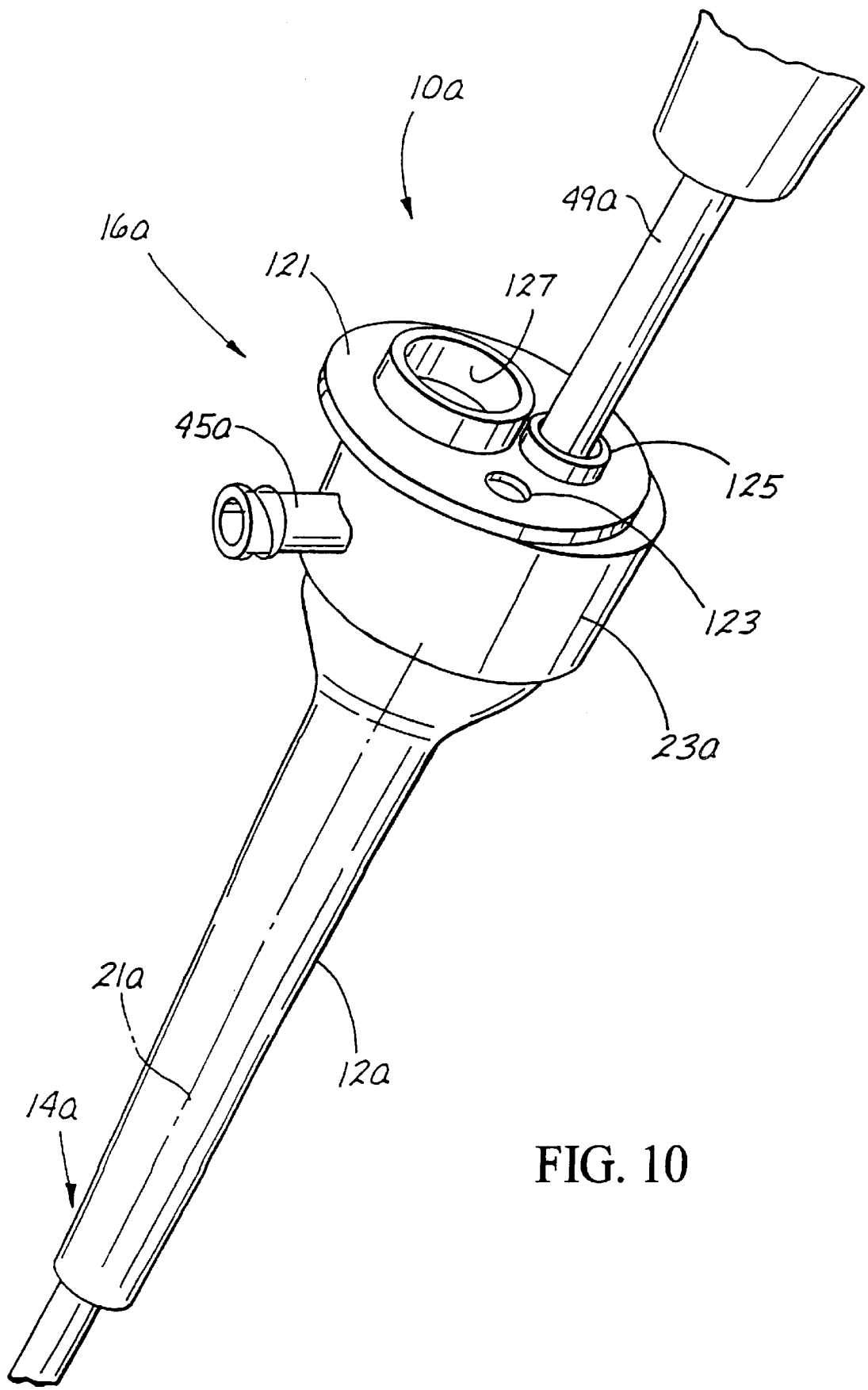
FIG. 10 is a perspective view illustrating an instrument inserted into a trocar comprising a further embodiment of the invention.

A further embodiment of the invention is illustrated in the perspective view of FIG. 10. In this embodiment, structures similar to those previously discussed will be designated with the same reference numeral followed by the lower case letter "a". Thus in FIG. 10, the trocar 10a includes a cannula 12a, having a distal end 14a and a proximal end 16a, and a valve housing 23a which partially defines a housing cavity 30a. The trocar 10a also includes the insufflation tube 45a and is illustrated in combination with a retractor 49a which is representative of various surgical instruments. Both the cannula 12a and the valve housing 23a are aligned along the axis 21a of the trocar 10a.

In the embodiment of FIG. 10, the housing cavity 30a is also partially defined by an end cap 121 which is movable transverse to the axis 21a at the proximal end 16a. The end cap 121 includes access ports 123–127 which provide access for small, medium and large diameter instruments, respectively, into a working channel 41a of the trocar 10a.

Reference to the exploded view of FIG. 11 will show that the trocar 10a also includes a valve assembly 46a and a partition structure 130. Another feature associated with this embodiment is the modularity of construction which provides for a quick disconnect between the cannula 12a and the remainder of the trocar including the valve housing 23a and the valve assembly 46a. This quick disconnect in the illustrated embodiment takes the form of a bayonet connection including tabs 132 and associated slots 134.

The concept of modularity offers several advantages to this embodiment of the invention. For example, if a different seal assembly 46a is desired for a particular trocar, lo that assembly with its housing 23a can be replaced without removing the cannula 12a from its operative site. This same feature permits the replacement of a valve assembly 46a which has been torn or is otherwise inoperative. The quick release separation between the housing 23a and cannula 12a also facilitates rapid and complete desufflation of the abdominal cavity.

The cannula 12a of this embodiment extends from the distal end 14a to an enlarged proximal portion 136 having a proximal facing end surface 138. The valve housing 23a has a lower skirt 141 which is sized to receive the proximal portions 136 of the cannula 12a. It is this skirt 141 which defines the slots 134 of the bayonet connection. Extending in the opposite direction from the skirt 141 is a sidewall 143 which extends proximally to an end surface 145. It is the side wall 143 together with the end cap 121 which define the housing cavity 30a.

Between the skirt 141 and the sidewall 143, an annular flange 147 extends inwardly providing a proximal facing surface 152 and a distal facing surface 154. An annular projection 156, which extends from the flange 147 toward the skirt 141, will be discussed in greater detail below.

The partition structure 130 includes a proximal end wall 161 having a proximal surface 163. Extending downwardly in FIG. 11 from the end wall 161, is a partition 165 which has a particular configuration discussed in greater detail below. The partition 165 extends to a bottom surface 167. Extending upwardly from the surface 163 of the end wall 161 are a plurality of buttons 170 which facilitate a snap fit relationship between the partition structure 130 and the end cap 121.

The valve assembly 46a is similar to that previously disclosed in its inclusion of multiple valve sets each having a septum valve which is defined in an end wall 172 having a proximal surface 174. Extending downwardly in FIG. 11 from the end wall 172 is a sidewall 176 and an inwardly extending shoulder 178 having a distal facing surface 181. A cylindrical annulus 183 extends axially from the shoulder 178 to a distally facing surface 187. This surface 187 is extended radially outwardly by a flange 185.

The end cap 121 has a generally planar configuration defined by a wall 190 having a distally facing surface 192. Extending upwardly from the wall 190 are a plurality of cylinders 194 and 196 which aid in aligning the instruments and protecting the septum valve formed in the end wall 172 of the valve assembly 46a. Extending downwardly in FIG. 11 from the end wall 190 is an annulus 198 which functions to prevent deformation of the zero-closure valve. Also extending downwardly from the end wall 190 are a plurality of male components 197 which register with the female projections 170 in a snap fit relationship.

These various components of FIG. 11 are also illustrated in the assembled view of FIG. 12. Of particular interest in this view are the relationships among the flange 185 of the valve assembly 46a, the flange 147 of the housing 23a, and the surface 138 of the cannula 12a. In this construction, the flange 185 is sandwiched between the surface 138 of the cannula 12a and the surface 154 of the flange 147. It is this combination which automatically forms a seal between the valve assembly 46a, the housing 23a and the cannula 12a. The seal is enhanced by the projection 156 on the flange 147 which increases the sealing relationship between the flange 147 and the elastomneric flange 185.

The interrelationships of the various components of the trocar 10 can be best understood with reference to the assembled view of FIG. 12. Initially a subassembly can be formed between the end cap 121, the valve assembly 46a and the partition structure 130. In the preferred method of assembly the partition structure 130 is inserted through the opening at the bottom of the valve assembly 46a where the partition 165 extends around the zero-closure valves of the assembly. The proximal end wall 161 of the structure 130 is brought into contact with the end wall 172 of the valve assembly 46a. With the projections 170 of the structure 130 extending through concentric holes in the end wall 172.

Figure 14:
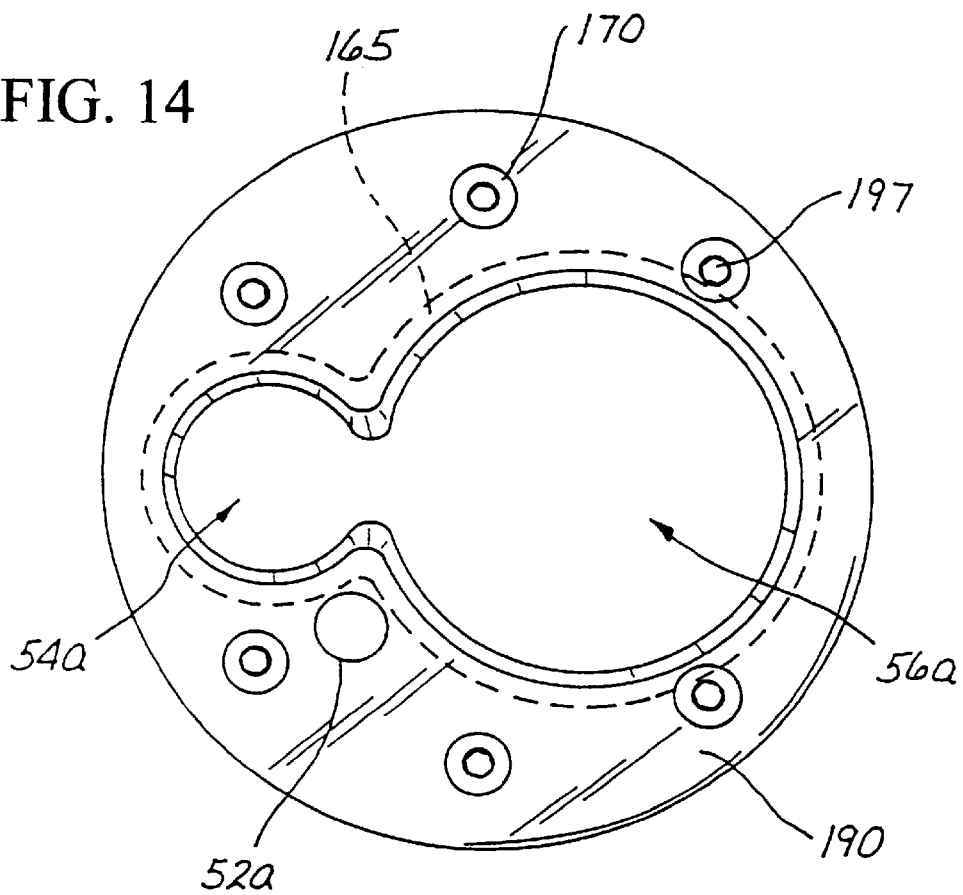
FIG. 14 is a top plan view of the partition structure of FIG. 11.

With the partition structure 130 operatively positioned within the valve assembly 46a, the end cap 121 can be moved into position over the top of the valve structure 46a. In this step, the projections 197 of the end cap 121 extend into the buttons 170 associated with the partition structure 130 preferably in a snap fit relationship. This snap fit completes the subassembly by maintaining the end wall 190 of the end cap 121, the end wall 172 of the valve assembly 46a, and the end wall 161 of the partition structure 130 in a generally fixed relationship. The resulting top view of the subassembly is best illustrated in FIG. 14. In this view, the valve sets are not shown in detail, but nevertheless are represented by their reference numerals 52a, 54a and 56a.

The subassembly including the end wall 121, the valve assembly 46a, and the partition structure 130 can then be mounted in the housing 23a. This is accomplished in the preferred method by introducing the end of the subassembly including the structure 130 into the top of the housing 23a until the surface 192 of the end wall 190 on the end cap 121 is brought into contact with the proximal surface 145 of the side wall 143. Since the end wall 190 is larger in diameter than the hole at the proximal end of the housing 23a, the end cap 121 cannot pass further into the housing cavity 30a.

A particularly advantageous feature of the present invention biases the end cap 121 in this sliding contact relationship with the surface 145 of the housing 23. This bias is obtained by stretching or tensioning the side walls 176 of the valve assembly 46a. With the end cap 121 fixed axially in the proximal direction, the stretched configuration of the sidewalls 176 can be maintained by fixing the distal end of the valve assembly 46a axially in the distal direction with the sidewall 176 stretched therebetween. In a preferred embodiment the distal end is fixed by fitting the outwardly extending annular flange 185 of the valve assembly 46a over the inwardly extending annular flange 147 associated with the housing 23a. In this step, the distally facing surface 181 of the valve assembly 46a is also brought into contact with the proximal facing surface 152 of the housing 23a. The interlocking relationship of the flange 147 and 185 is assisted by the projection 156 on the annular flange 147 and a similar projection on the flange 185.

To further maintain the fixed relationship of the flanges 185 and 147, the cannula 12a can be introduced distally into the channel defined by the skirt 141. This brings the proximal surface 138 of the cannula 12a into abutting relationship with the distally facing surface 187 of the valve assembly 46a. It also sandwiches the elastomeric flange 185 between the surface 154 of the flange 147 and the surface 138 of the cannula 12a. This not only maintains the elastomeric flange 185 in a fixed relationship with the housing 23a and cannula 12a, but also enhances formation of seals between these adjacent elements. As previously discussed, the cannula 12a can be held in its operative position by a quick disconnect structure such as the bayonet fitting formed between the tabs 132 and slots 134.

Once the trocar 10 has been assembled, the operative features of the concept become readily apparent. One of these features has to do with the floating relationship between the seal sets, such as the set 54a and 56a illustrated in FIG. 13. This floating of the seal sets in order to accommodate the off-axis insertion of instruments was first disclosed by Ritchart et al in U. S. Patent No.

Figure 13:
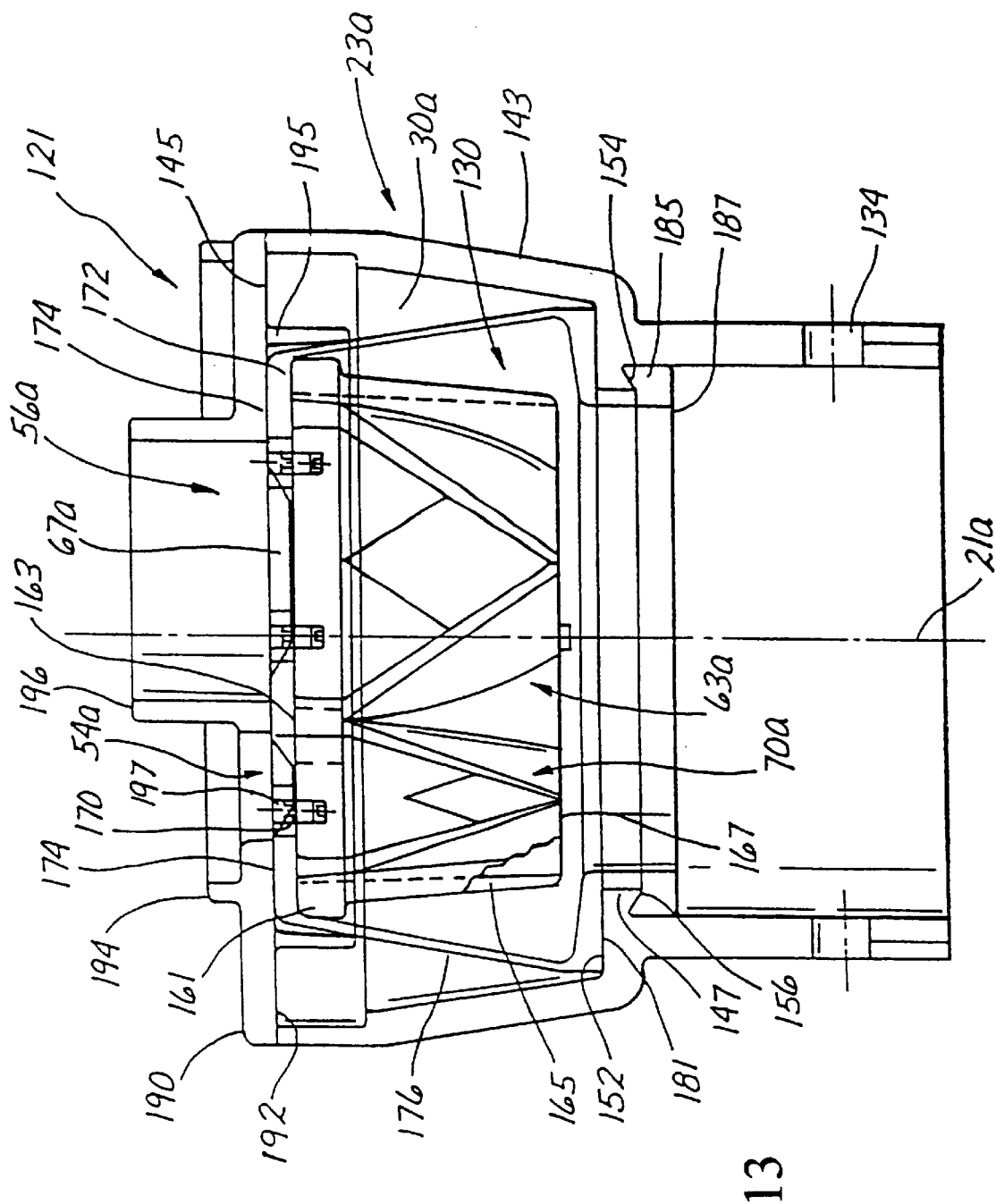
FIG. 13 is an axial cross-section view of the partition structure illustrated in FIG. 11.

In the embodiment of FIG. 13, floating of the seal sets 54a and 56a is facilitated by permitting the end cap 121 to move transverse to the axis 21a in sliding engagement with the side wall 143 of the housing 23a. While this floating movement of the end cap 121 could be accomplished in an enlarged recess, as taught by Ritchart et al, the size of the housing 23a can be reduced if the end cap 121 is permitted to define the largest diameter of the trocar 10 at its proximal end. In this case, the outside diameter of the side wall 143 of the housing 23a does not exceed the diameter of the end cap 121.

While the end cap 121 is permitted to float laterally or radially of the housing 23a, this float may be limited in order to protect the valve sets 54a, 56a. In the illustrated embodiment, this protection is afforded by the annulus 98 which extends into the valve cavity 30a. As the end cap 121 moves laterally, the annulus 198 approaches the sidewall 143 and eventually reaches a point of interference where the end cap 121 cannot be further laterally displaced. Thus the annulus 198 ensures that operation of the seals 54a and 56a is not inhibited by extensive lateral movement of the end wall 121.

The medium seal set 54a (including the septum valve 67a and zero-closure valve 70a) and the large seal set (including the septum valve 61 a and zero-closure valve 63a may also benefit from additional isolation. In a typical situation, an instrument will be inserted through one of the seal sets, such as the set 54a, where the associated septum valve forms a seal with the instrument. In this particular valve set, the zero-closure valve 70a will be open and non-sealing as long as the instrument is in place. The concern at this point is with the operation of the zero-closure valve 63a associated with the other valve set. If the instrument is allowed to tilt or is otherwise brought into contact with the zero-closure valve 63a, associated with the other valve set 56a, that valve 63a can be deformed resulting in leaking of the insufflation gas.

Figure 15:
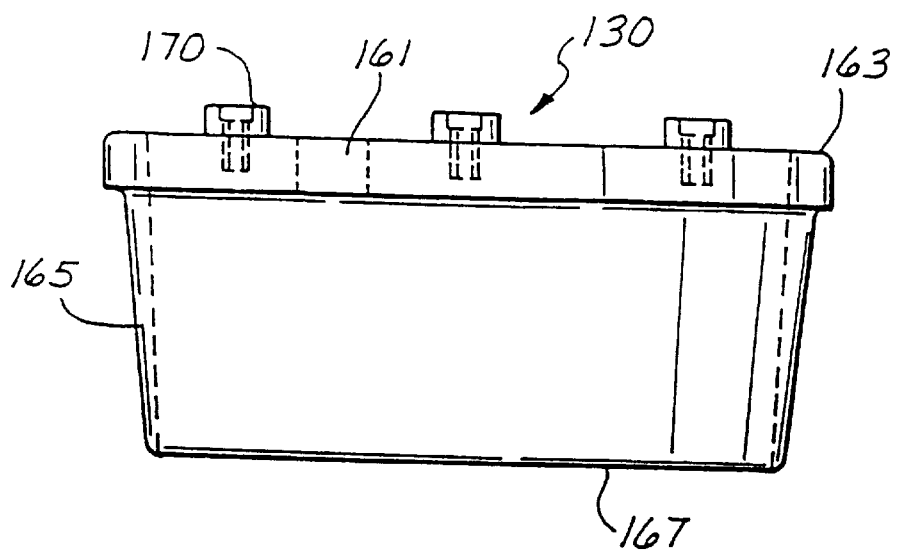
FIG. 15 is an enlarged side elevation view of the partition structure of FIG. 11.

To prevent this leakage and deformation, it is desirable to isolate the zero-closure valves 63a and 70a to some extent, from each other. This is the function of the partition 165 in the structure 130. This partition 165 extends generally around each of the zero-closure valves 63a and 70a associated with the valve sets 56a and 54a, respectively. When these zero-closure valves 63a and 70a are formed in close proximity to each other for example with their respective axes separated by less than the sum of their radii, the partition 165 may be slightly broken immediately between the zero-closure valves 63a and 70a. In this case, the partition 165 forms a continuous curtain around the valve sets 54a and 56a typically in the shape of a figure eight as best illustrated in FIG. 15.

Figure 8:
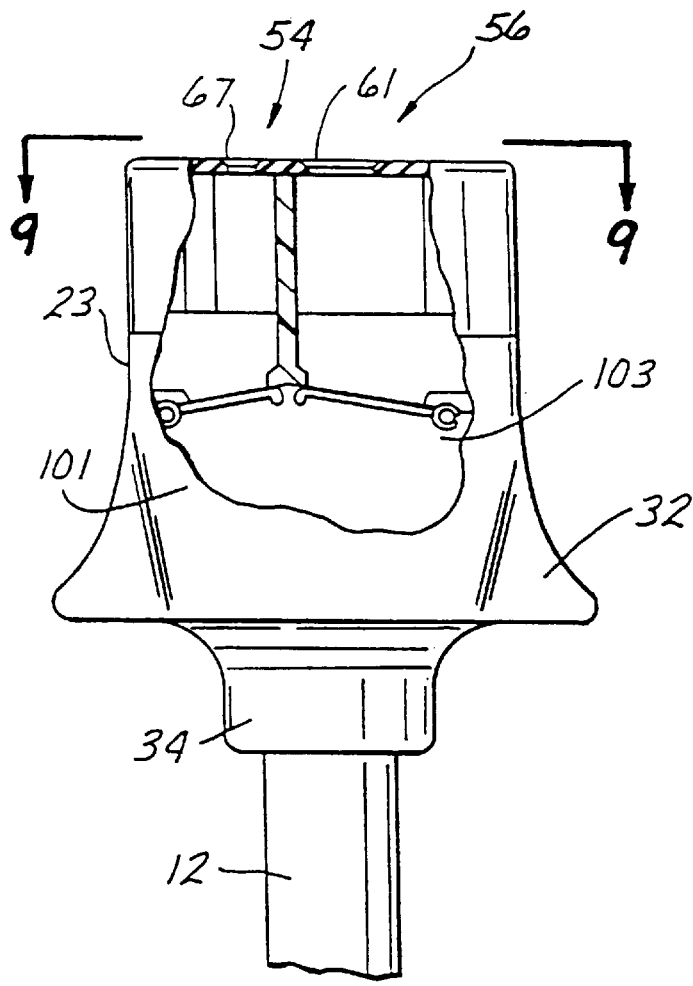
FIG. 8 is a side view partially in section of the trocar illustrating a flapper valve having zero-closure characteristics in a further embodiment of the invention.
Figure 9:
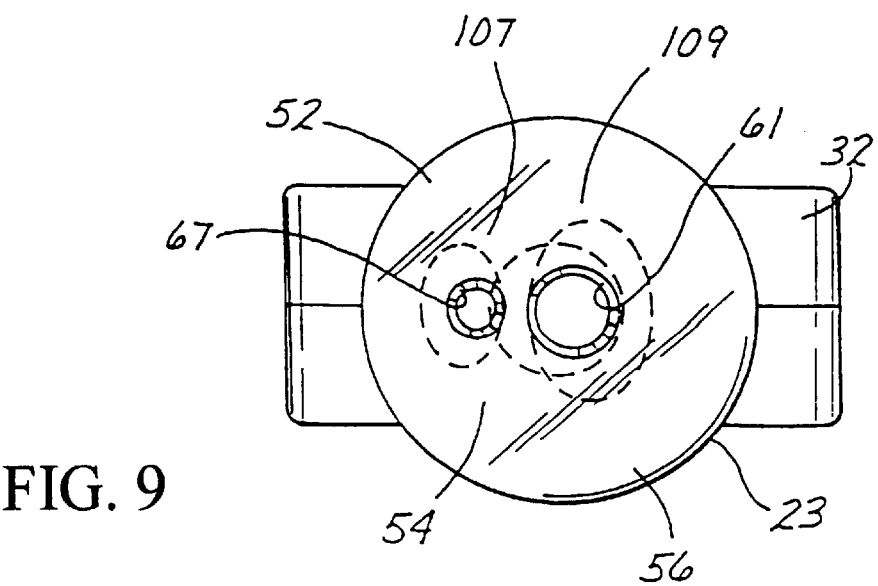
FIG. 9 is a top plan view taken along lines 9—9 of FIG. 8.

From the foregoing discussion it is apparent that the trocar 10 of this invention can accommodate all sizes of instruments from the smallest instrument, such as the catheter 48, to the largest instrument, such as the obturator 50, which can pass through the associated cannula 12. Multiple septum valves 58, 67 and 61 can be formed in any transverse wall disposed interiorly of the valve housing 23 or at the end wall 38 of the elastomeric housing portion 27. These septum valves 58, 67 and 61 can be formed at different distances from the central axis 21 in the manner previously discussed. For each of the larger valve sets, for example the medium valve set 54a and large valve set 56a, a zero-closure valve may be required. These valves, such as the zero-closure valves 70a and 63a, can be provided in any form associated with the prior art. Double duck bill valves such as those illustrated in FIGS. 1–7 are particularly appropriate for this concept. However, a separate flapper valve, such as those designated by the reference numerals 107 and 109 in FIGS. 8 and 9 can be provided for the respective valve sets 54 and 56.

In a particularly desirable embodiment, the end cap 121 can be formed in sliding engagement with the housing 23a. This embodiment is enhanced by the small size of the housing 23a which is not greater than the diameter of the end cap 121. The valve assembly 46a can be stretched to maintain the end cap 121 in sliding engagement with the housing 23a. The annulus 98 can be formed to uniformly limit the lateral displacement of the end cap 121 relative to the housing 23a. The partition 165 further protects the zero-closure valves 63a and 70a from interference due to operation of an adjacent valve set. The modular concept permits the cannula 12a to be separated from the housing 23a while at the same time providing a quick disconnect fitting which will function to enhance the seal between the valve assembly 46a and the housing 23a.

Figure 16:
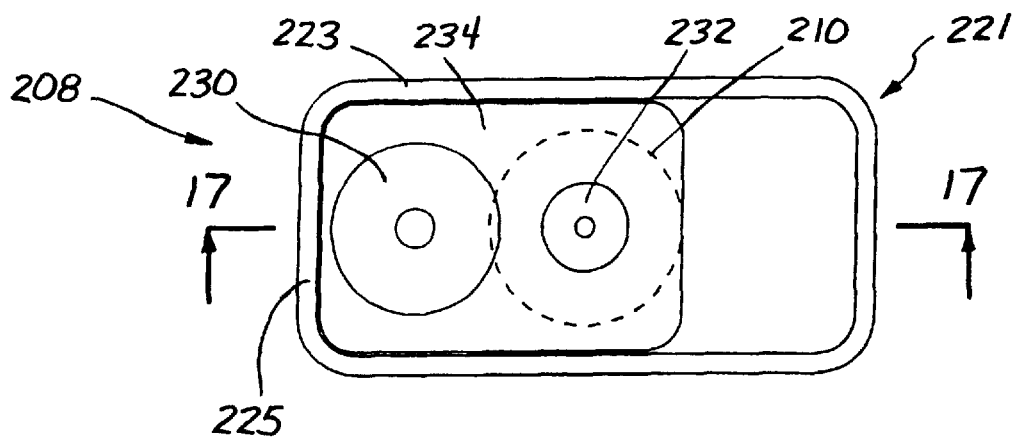
FIG. 16 is a top-plan view of a further embodiment of the invention having a seal housing with a rectangular configuration, and a floating septum disposed in a first position to accommodate a small instrument.
Figure 17:
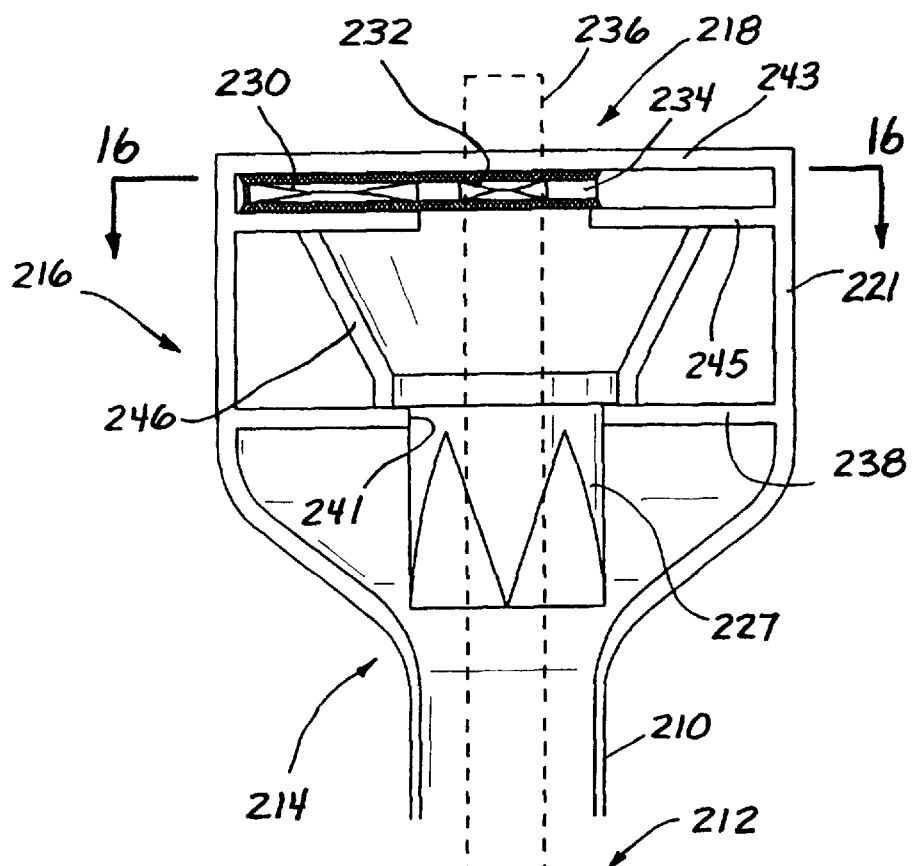
FIG. 17 is an axial cross-section view taken along lines 17—17 of FIG. 16.

A further embodiment of the invention is illustrated in the top-plan view of FIG. 16 and the associated cross-sectional view of FIG. 17, where a trocar is designated by the reference numeral 208. This embodiment of the trocar 208 includes a cannula 210 having a distal end 212 and a proximal end 214. A valve housing 216 is disposed at the proximal end 214 and defines a working channel 218 with the cannula 210. The valve housing 216 in this embodiment has rigid walls 221 which in radial cross-section have the shape of a polygon, such as a square or rectangle, as best illustrated in FIG. 16. The rectangle in this embodiment has a long-side 223 extending in one direction, and a short side 225 extending in a second direction generally perpendicular to first direction.

Disposed within the valve housing 216 are a plurality of valves, for example, a zero-closure valve 227 and a pair of septum valves 230 and 232, the latter being formed in a septum 234. The zero-closure valve 227 has characteristics for receiving an instrument such as that illustrated by the dotted lines 236. In the absence of the instrument 236, the valve 227 forms a seal with itself, however, in the presence of the instrument 236, no seal is formed. Hence, this valve 227 is commonly referred to as a zero-closure valve.

The septum valves 230 and 232 are also adapted to receive the instrument 236. However, by comparison, when the instrument 236 is not present, the septum valves 230 and 232 do not form a seal. It is only when the instrument 236 is present that the septum valves 230 and 232 form a seal with the cylindrical outer surface of the instrument 236.

The septum valves 230 and 232 are of different sizes and are adapted to accommodate different diameters of instruments. For example, the septum 232 is of a smaller size and, therefore, adapted to accommodate a small instrument 236, while the septum 230 is of a larger size and, therefore, adapted to accommodate a larger instrument 236'.

In this embodiment, the zero-closure valve 227 is mounted in axial alignment with the cannula 210. A partition 238, which extends between the walls 221 of the housing 216, is provided with a central aperture 241. The zero-closure valve 227 is mounted to extend through this aperture 221 in sealing engagement with the partition 238. A conical wall 246 can be provided to funnel the instrument 236 toward the zero-closure valve 227.

The septum 234 can be mounted between an end wall 243 of the housing 216, and a second partition 245 which also extends between the walls 221. These walls 243 and 245 form portions of the housing 216 which define a cavity 247 that is flat in configuration and generally perpendicular to the axis of the cannula 210. The septum 234 is disposed in this cavity 247 and, importantly, is free to float between the end wall 243 and the partition 245.

Figure 18:
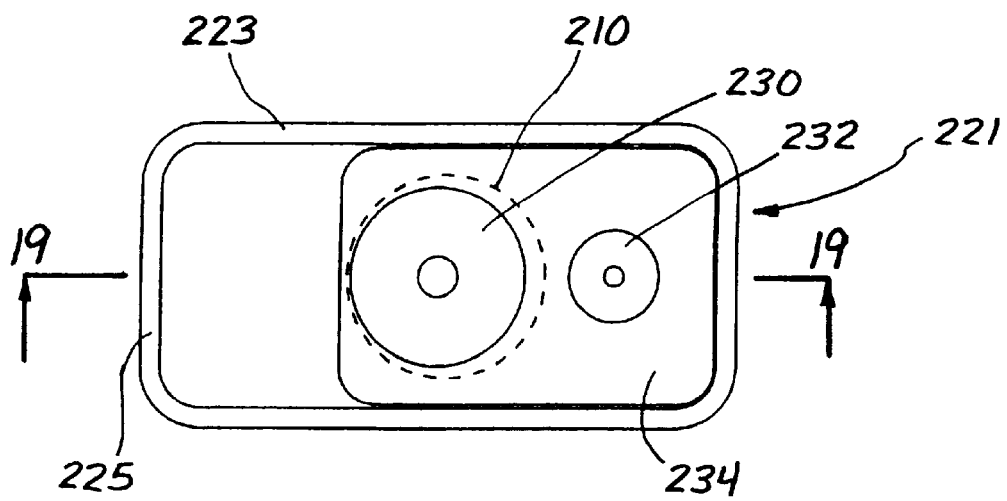
FIG. 18 is a top-plan view similar to FIG. 16 and illustrating the floating system in a second position to accommodate a large instrument.
Figure 19:
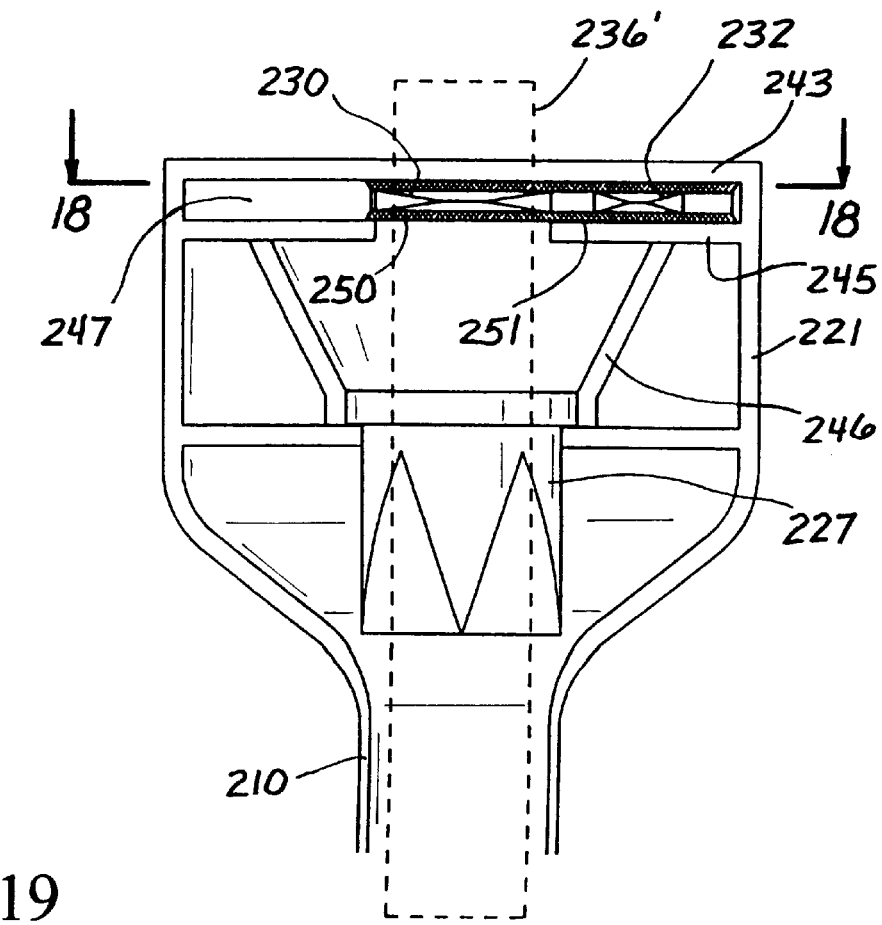
FIG. 19 is an axial cross-section view taken along lines 19—19 of FIG. 18.

In a preferred embodiment wherein the valve housing 216 has the configuration of a rectangle, the floating of the septum 234 that results in septum selection within the cavity 247 can be restricted to a single direction. For example, with reference to FIG. 16, it can be seen that the septum 234 is free to move in a first direction generally parallel to the long side 223, but is restricted from movement in a second direction generally parallel to the short side 225. By restricting the floating movement in the second direction, the septum 234 is easily shifted from a first location where the septum valve 232 is aligned with the zero-closure valve 227 as illustrated in FIGS. 16 and 17, to a second location wherein the septum valve 230 is aligned with the zero-closure valve 227 as illustrated in FIGS. 18 and 19. It will be noted that in this embodiment, flotation associated with septum valve selection can be restricted to a single direction. However, the flotation associated with instrument manipulation is free to occur in all directions.

In this embodiment of FIG. 16 wherein the zero-closure valve 227 is shared by the septum valves 230 and 232, a leakage condition can develop through the unused septum. Realizing that a positive air pressure exists within the cannula 210, it can be appreciated that this positive pressure is transferred to the septum 234 when the zero-closure valve 227 is open. Whereas the septum 234 may form a seal with the instrument 236 to prevent escape of this pressurized air, the other septum seal 230 would typically be in an open state thereby permitting the pressurized air to escape through the septum 234. In order to prevent blow-back in this embodiment, cup seals 250 and 251 can be formed around the septums 230 and 232, respectively, so that each one is isolated from the pressurized air when it is not in its operative position. For example, when the septum 234 is in the first location, as illustrated in FIG. 17, the cup seal 250 isolates the septum 230 from the pressurized fluid. In like manner, when the septum 234 is in the second location, the cup seal 252 isolates the septum seal valve 232 from the pressurized fluid, as illustrated in FIG. 19, by permitting fluid communication with only one septum at a time with the cannula.

A further embodiment of the trocar 208 is illustrated in FIGS. 20–23. In this embodiment, elements of structure which are similar to those disclosed with reference to the FIG. 16 embodiment are designated by the same reference numeral followed by the lower case letter "b". Hence, this embodiment includes the cannula 210b, and the walls 221b which form the valve housing 216b. The zero-closure valve 227b is mounted in the partition 238b, and the septum 234b is free to float between the end wall 243b and the second partition 245b.

Figure 20:
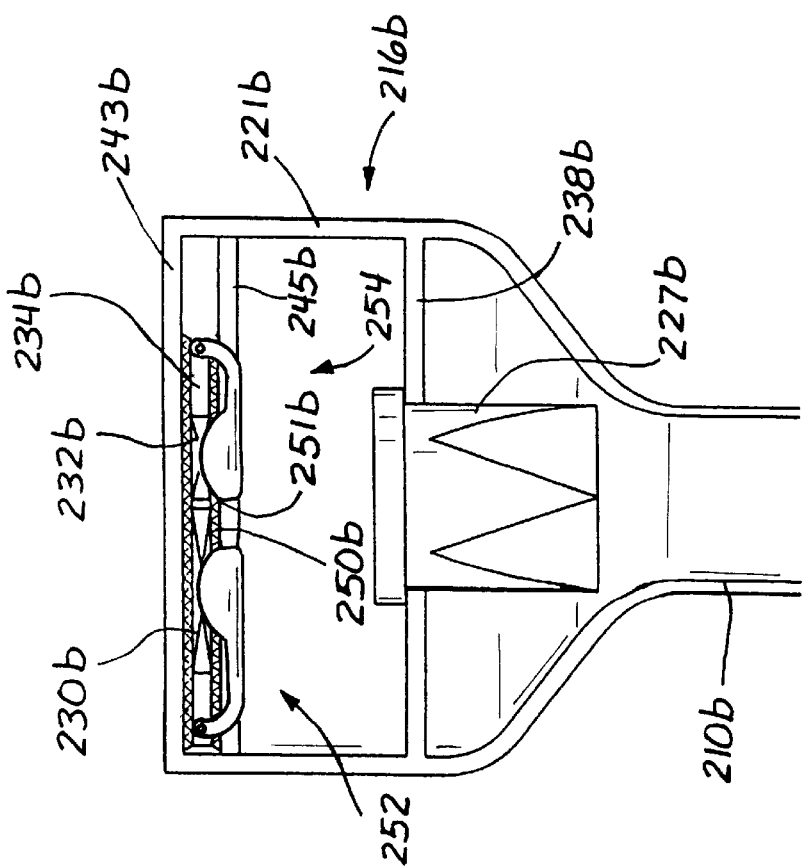
FIG. 20 is an axial cross-section view similar to FIG. 17 and illustrating an embodiment with a pair of check valves in a first location and a closed state.

In the embodiment of FIG. 20, the cup seals 250b and 251b associated with the septum valves 230b and 232b, respectively, can be augmented by a pair of check valves 252 and 254, respectively. In the illustrated embodiment, the check valve 252 is pivotal on the septum 234b and includes a blocking element 256 which is larger than the hole 230b in the septum 234b. Similarly, the check valve 254 is pivotal on the septum 234b and includes a blocking element 258 which is larger than the hole 232b in the septum 234b.

The check valves 252 and 254 can be mounted to pivot on the septum 234 or, alternatively, can be provided with elastomeric attachment members which permit the blocking elements 257 and 258, respectively, to move between a blocking position and an open position.

Figure 21:
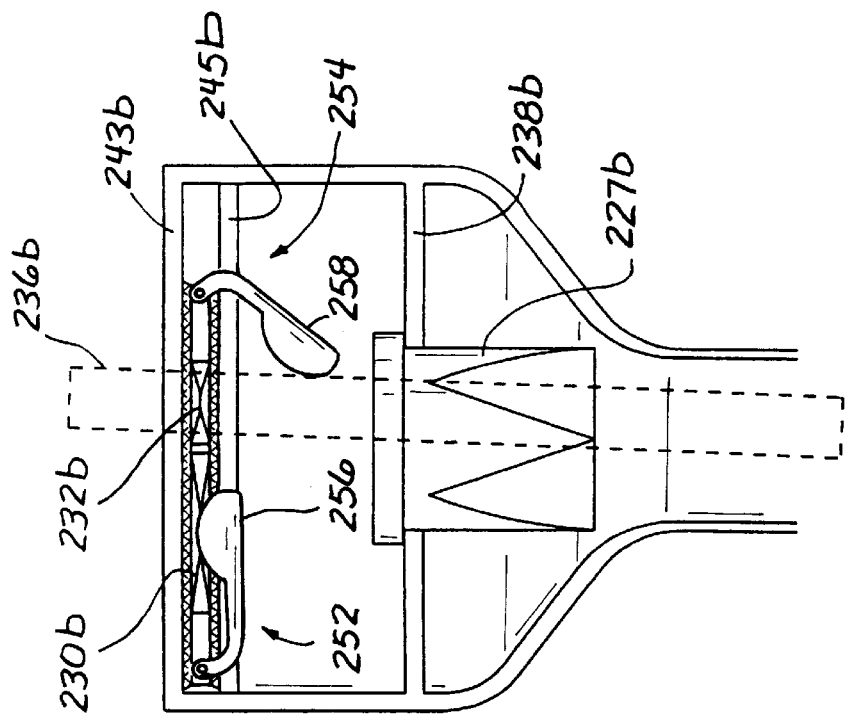
FIG. 21 is an axial cross-section view similar to FIG. 20 and showing one of the check valves moved to an open state by the small instrument.

Referring to FIG. 21, it can be seen that insertion of the instrument 236b through the septum 232b causes the check valve 254 to open and permit access to the zero-closure valve 227b. In this case, it will be noted that the opening of the zero-closure valve 227b by the instrument 236b exposes the septum 234b to the pressurized air. However, this air cannot escape through the septum valve 232b because of the seal formed around the instrument 236b. Nor can the air escape through the septum 230b because the blocking element 257 of the check valve 252 effectively blocks that valve 230b.

Figure 23:
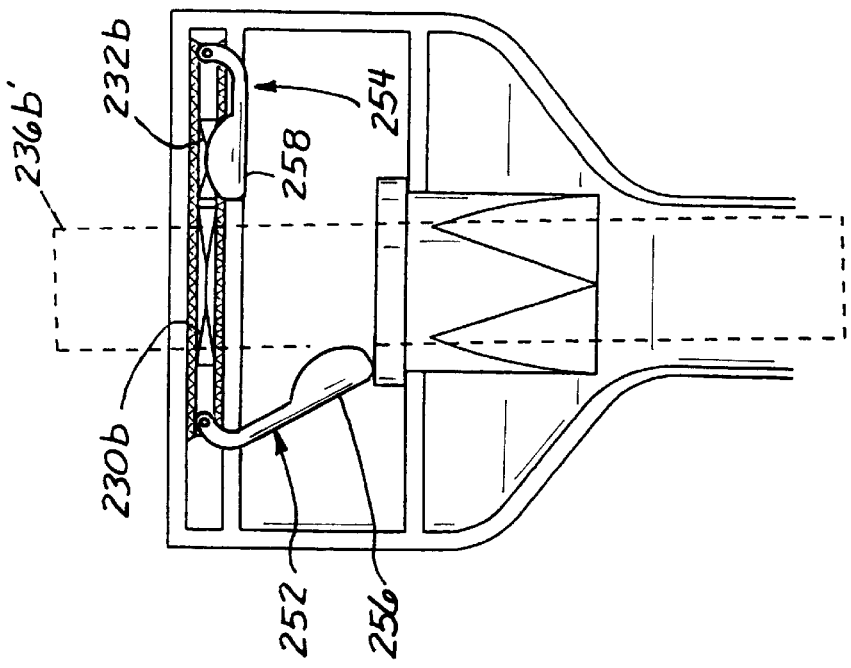
FIG. 23 is an axial cross-section view similar to FIG. 21 and illustrating one of the check valves moved to the open state by the large instrument.
Figure 22:
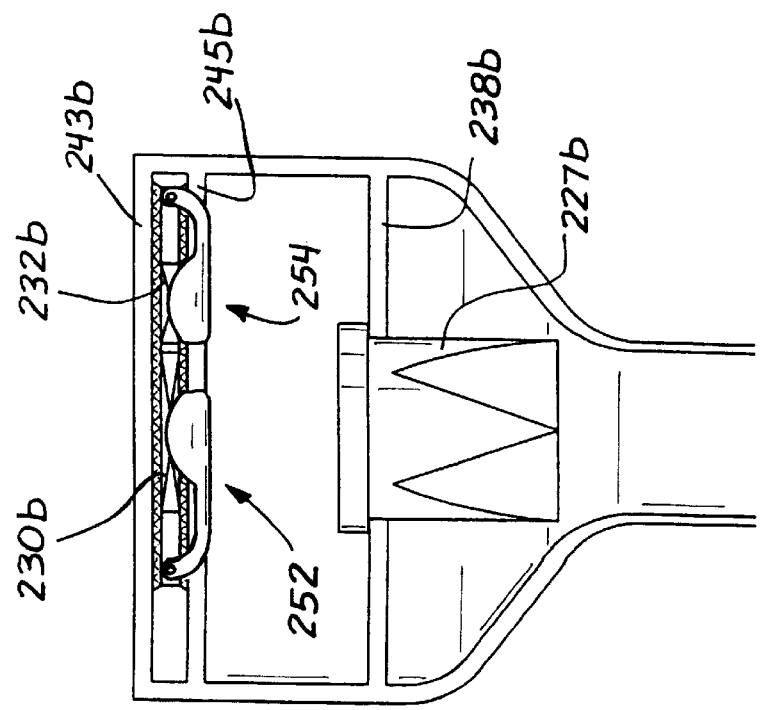
FIG. 22 is an axial cross-section view of the embodiment of FIG. 20 showing the septum valves in a second location and the closed state.

When the small instrument 236b is to be replaced with the larger instrument 236b', the septum 234b is initially moved or floated to the second location, as illustrated in FIG. 22. Then the larger instrument 236b' can be inserted, as illustrated in FIG. 23, opening the check valve 252 to gain access to the zero-closure valve 227b. As pressurized fluid is exposed to the septum 234b, it is maintained within the housing 216b by a seal formed between the septum valve 230b and the instrument 236b'. Blow-back through the smaller septum valve 232b is prevented by the check valve 254, which forms a seal with the blocking element 258.

Figure 25:
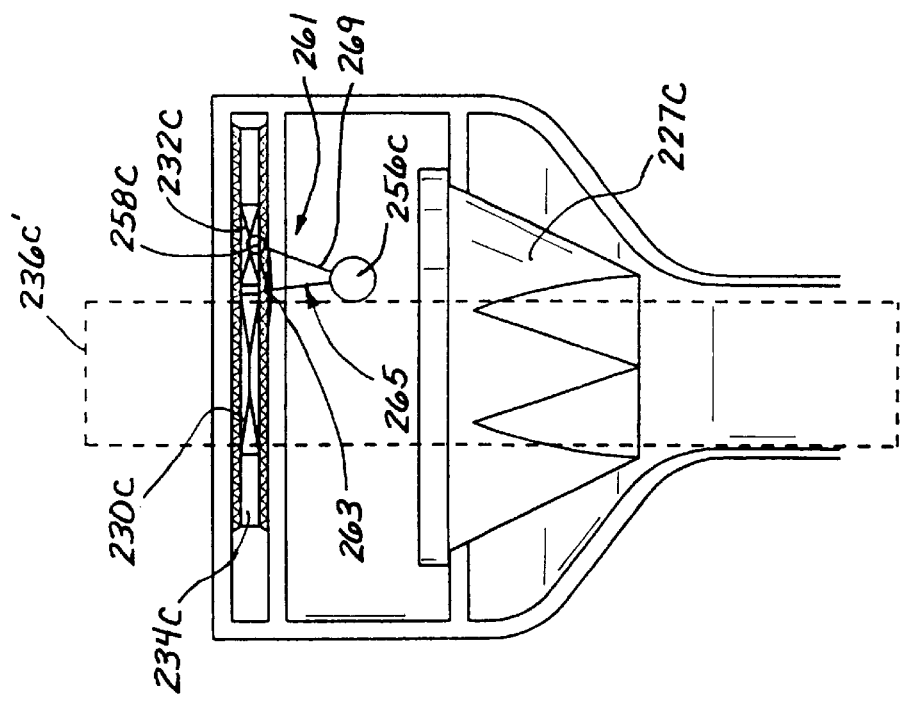
FIG. 25 is an axial cross-section view similar to FIG. 24 wherein the reciprocating valve is tripped to a second position by operation of the large instrument.
Figure 24:
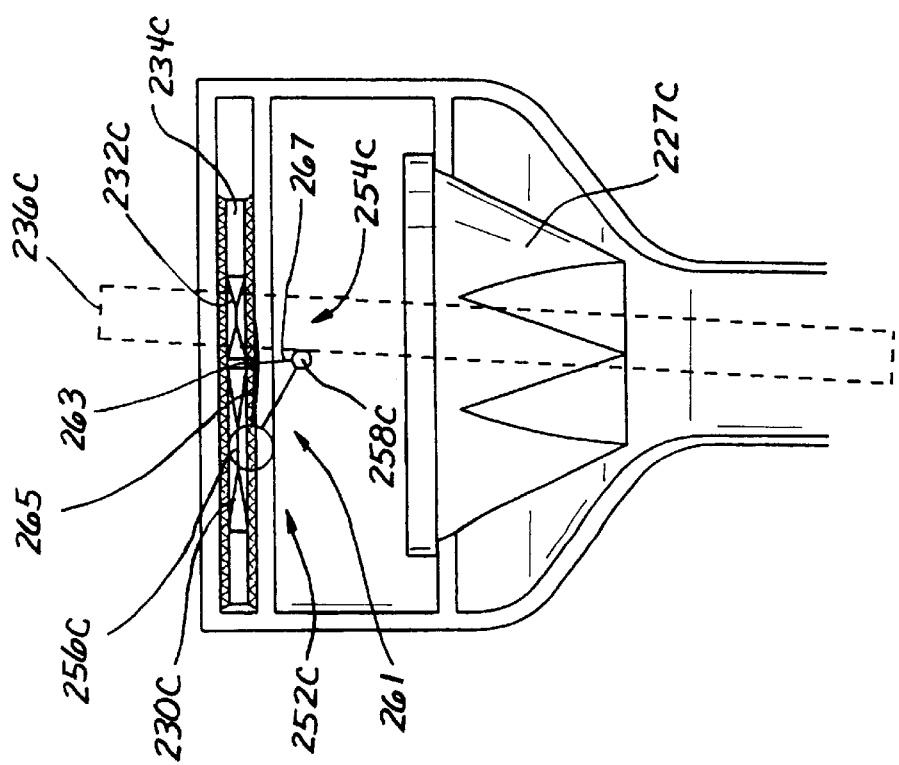
FIG. 24 is an axial cross-section view similar to FIG. 20 wherein the check valves are coupled as a single reciprocating valve disposed in a first position by the small instrument.

In a further embodiment of the invention, illustrated in FIGS. 24 and 25, elements of similar structure are designated by the same reference numeral followed by the lower case letter "c". This embodiment differs from that of FIG. 20 in that the check valves 252c and 254c do not operate independently, but rather function as a toggle or reciprocating valve 261. In this case, the reciprocating valve 261 pivots on the septum 234c at a fulcrum 263. The check valve 252c has a lever arm 265 which carries the blocking element 256b in a pivotal relationship with the fulcrum 263. In like manner, a lever arm 267 carries the blocking element 258c in a pivotal relationship with the fulcrum 263. A connecting arm 269 can be provided between the blocking elements 256c and 258c. In this embodiment, insertion of the instrument 236c not only opens the septum valve 232c, but it pivots the reciprocating valve 261 about the fulcrum 263, automatically moving the element 257c into a blocking relationship with the septum valve 230c, as illustrated in FIG. 24. Similarly, as illustrated in FIG. 25, insertion of the larger instrument 236c' through the septum valve 230c pivots the reciprocating valve 261 about the fulcrum 263 automatically moving the element 258c into a blocking relationship with the septum valve 232c.

A comparison of the check valve embodiment of FIG. 20 and the reciprocating valve embodiment of FIG. 24 will highlight the advantages of these respective combinations. For example, it will be noted that in the FIG. 20 embodiment, the check valves 252 and 254 operate independently. The open or closed state of the check valve 252, for example, is not dependent upon the open or closed state of the check valve 254.

By comparison, the reciprocating valve 261 of FIG. 24 operates such that the position of the blocking element 256c is dependent upon the position of the blocking element 258c. For example, as the blocking element 258c is moved to the open position by the instrument 236c, as illustrated in FIG. 24, the blocking element 257c is simultaneously moved to the closed position. Similarly, when the blocking element 257c is moved to the open position by the instrument 236c', as illustrated in FIG. 25, the blocking element 258c is simultaneously moved to the closed position.

As a further distinction, it will be noted that the check valves 252 and 254 in FIG. 20 are individually biased to the closed position. This may not be the case with the reciprocating valve 261 which can rely upon the force of instrument insertion to move the respective blocking members 256c and 258c to their closed positions. Alternatively, the reciprocating valve 261 can include an over-center device so that the blocking elements 257c and 258c are alternatively biased to their closed positions. Nevertheless, the blocking elements 257c and 258c will tend to move in unison, that is, with one of the blocking elements, such as the element 257c, moving toward the closed position, and the other of the blocking elements, such as the element 258c, moving toward the open position. Notwithstanding this tendency to move in unison, the blocking elements 257c and 258c may not have a rigid, fixed relationship. In such an embodiment, the connecting arm 269 may have some elastic characteristics permitting slight relative movement between the blocking elements 257c and 258c.

It is also contemplated that the valve 261 could be toggled, not by instrument insertion, but rather by movement of the septum 234c between its first and second locations. In such an embodiment, lateral movement of the septum would toggle the valve 261 to open one of the septum valves 230c and 232c, and close the other of the septum valves 232c and 230c, respectively.

Figure 27:
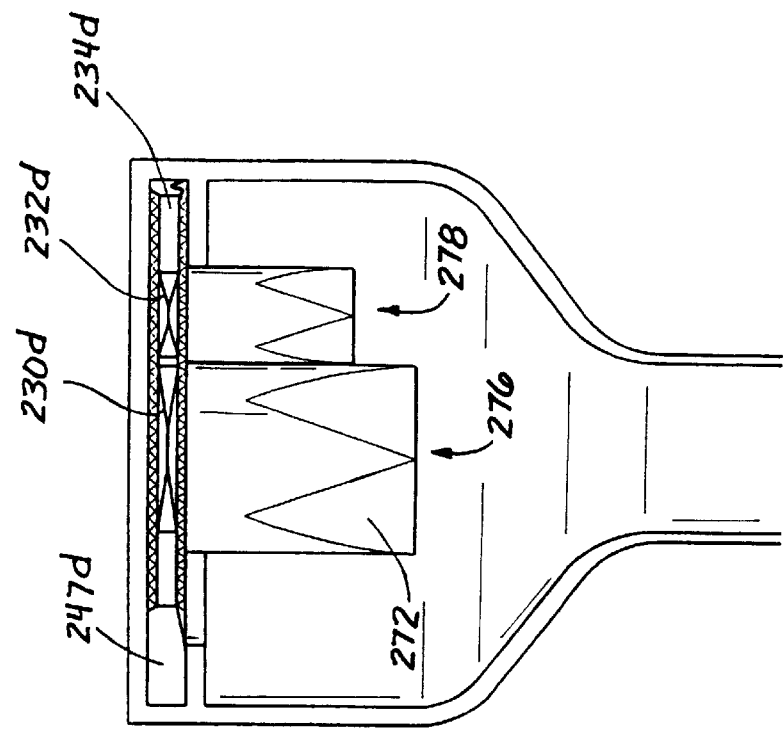
FIG. 27 is an axial cross-section view similar to FIG. 25 and illustrating the floating valve assemblies in a second location.
Figure 26:
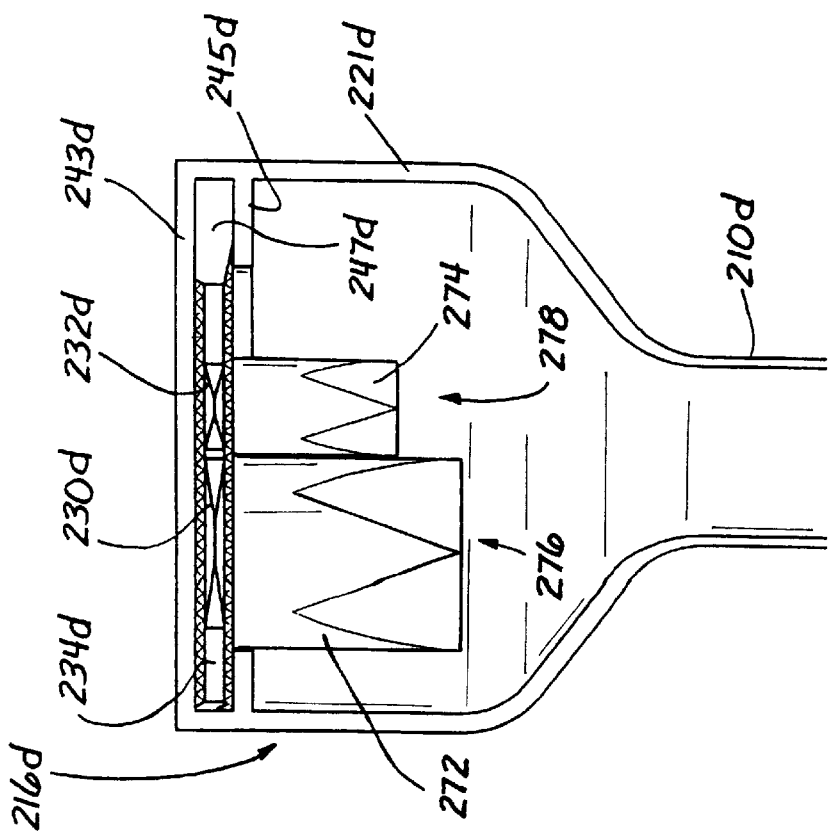
FIG. 26 is an axial cross-section view similar to FIG. 17 and illustrating an embodiment including multiple floating seal assemblies each including a septum valve and an associated zero-closure valve, the assemblies being illustrated in a first location.

In a further embodiment, illustrated in FIGS. 26 and 27, elements of structures similar to those described with reference to FIGS. 16–24 are designated by the same reference numeral followed by the lower case letter "d". Thus, this embodiment includes the cannula 210d, the valve housing 216d with walls 221d, the end wall 243d, and the partition 245d. The septum 234d is free to move to accommodate both types of flotation, that associated with septum selection, as well as that associated with instrument manipulation. This embodiment also includes the large septum valve 230d and the smaller septum valve 232d. However, in this case, each of these septum valves is combined with an associated zero-closure valve 272 and 274 to form separate valve assemblies 276 and 278. Each of the zero-closure valves 272 and 274 is coupled to the septum 234d, and therefore moves with the septum 234d as it floats within the cavity 247d.

In such an embodiment each septum valve, and its associated zero-closure valve, is alternatively moved to an operative position in general alignment with the cannula 210d. For example, in the first location, illustrated in FIG. 26, the valve assembly 278, including the septum valve 232d and the zero-closure valve 274, are in an operative position generally aligned with the cannula 210d. However, when the septum 234d is moved to the second location, as illustrated in FIG. 27, the second valve assembly 276, including the septum valve 230d and the associated zero-closure valve 272, are moved to the operative position in general alignment with the cannula 210d.

It can be appreciated that with such an embodiment, including two valve assemblies each with its own zero-closure valve, blow-back is not a significant problem. When an instrument is inserted into one of the valve assemblies, such as the assembly 278, pressurized air is not free to escape through the other septum valve, such as the valve 230d, because it has its own zero-closure valve, in this instance the valve 272, to prevent blow-back.

Figure 29:
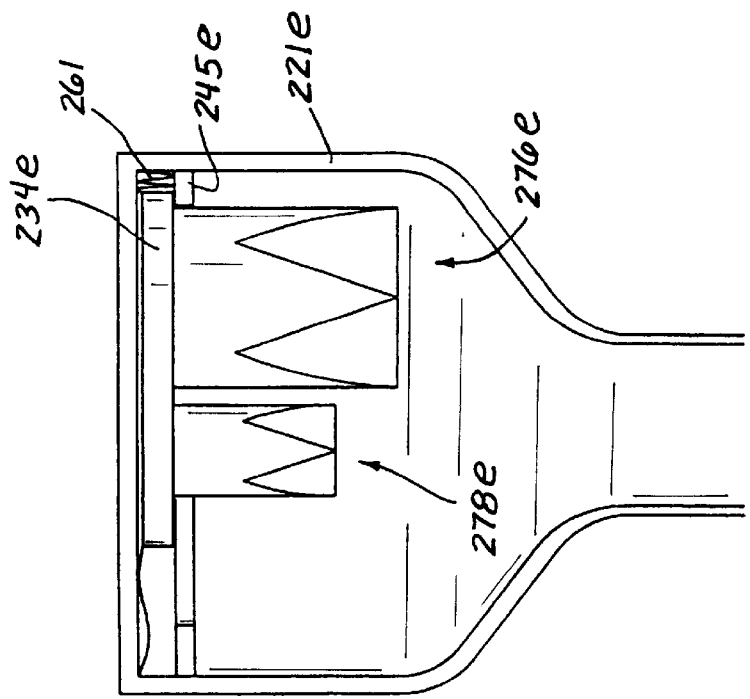
FIG. 29 is an axial cross-section view similar to FIG. 27 and illustrating the valve assemblies in the second location.
Figure 28:
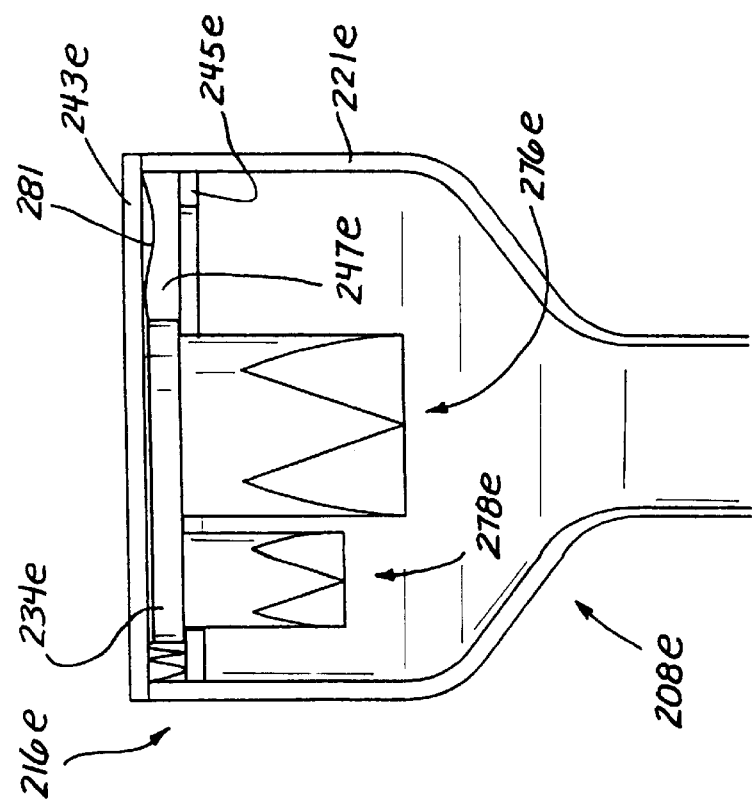
FIG. 28 is an axial cross-section view of a further embodiment having a skirt flexibly connected between the septum and the housing in a septum chamber, with the valve assemblies illustrated in the first location.

The escape of pressurized air around the septum 234 has already been discussed with reference to FIG. 17. In that embodiment, the cup seals 250 and 252 were mentioned as one alternative. Another alternative is illustrated in FIG. 28 wherein elements of similar structure are designated by the same reference numeral followed by the lower case letter "e". In this embodiment, a skirt 281 can be connected between the perimeter of the septum 234e and the walls 221e, forming the valve housing 216e. With this configuration, pressurized air that might extend beyond the partition 243e into the cavity 247e would be maintained within the trocar 208e by the skirt 281. With the skirt 281 having impermeable but flexible characteristics, this pressurized air is retained regardless of the position of the septum 234e. The pressurized air is maintained within the housing 216e, whether the septum 234e is in the first location as illustrated in FIG. 28, or the second location as illustrated in FIG. 29. The skirt 261, therefore, provides the same sealing function as either, or both, of the sealing portions of the cup seals 250 and 252 of FIGS. 17 and 19.

Figures 30, 31:
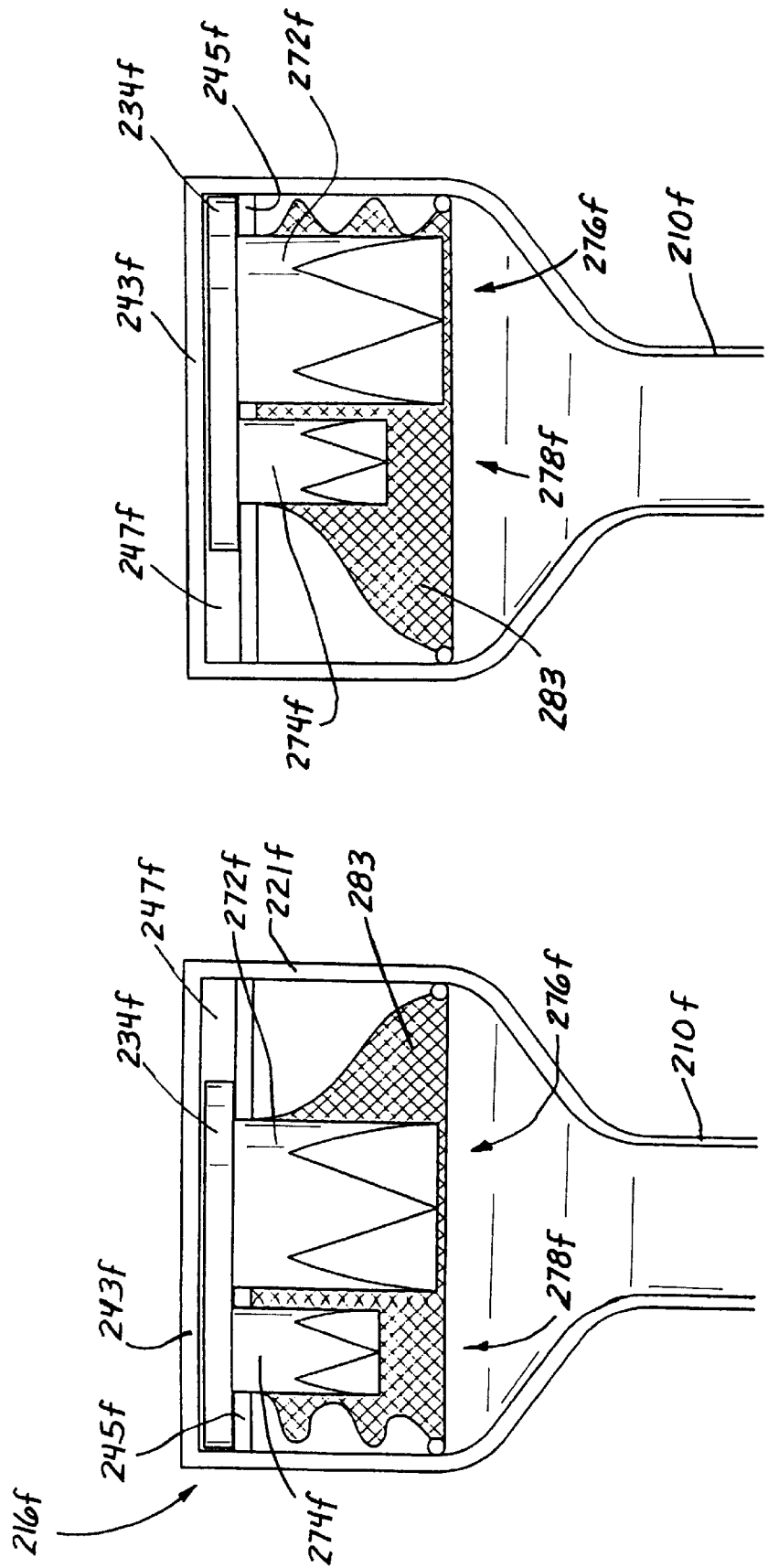
FIG. 30 is an axial cross-section view of a further embodiment wherein the skirt is disposed in a primary chamber of the housing and coupled between the zero-closure valves and the walls of the housing, with the valve assemblies disposed in the first location.
FIG. 31 is an axial cross-section view similar to FIG. 29 with the valve assemblies disposed in the second location.

Another skirt embodiment is illustrated in FIGS. 30 and 31 where elements of structure similar to that previously discussed are designated with the same reference numeral followed by the lower case letter "f". Thus, this embodiment includes the cannula 210f, the valve housing 216f with walls 221f, as well as the end wall 243f and partition 245f which form the cavity 247f. The valve assemblies 276f and 278f are free to float with the septum 234f as it moves within the cavity 247f.

A skirt 283 is provided and attached to the perimeter of each of the zero-closure valves 272f and 274f. From this location, the skirt 283 extends outwardly to engage the walls 221f distally of the partition 245f. In such an embodiment, air pressure within the cannula 210f is maintained distally of the cavity 247f, not only by the zero-closure valves 274f and 276f, but also by the skirt 283. In this embodiment, the cavity 247f and the septum 234f are never exposed to the pressurized air. This is true regardless of the position of the septum 234f. For example, in FIG. 30, the cavity 247f is isolated from pressurized air with the septum 234f in the first location. When the septum 234f is moved to the second location, as illustrated in FIG. 30, the cavity 247f remains isolated from the pressurized air. As in the previous embodiment, the skirt 283 is preferably both flexible and impermeable.

Figure 32:
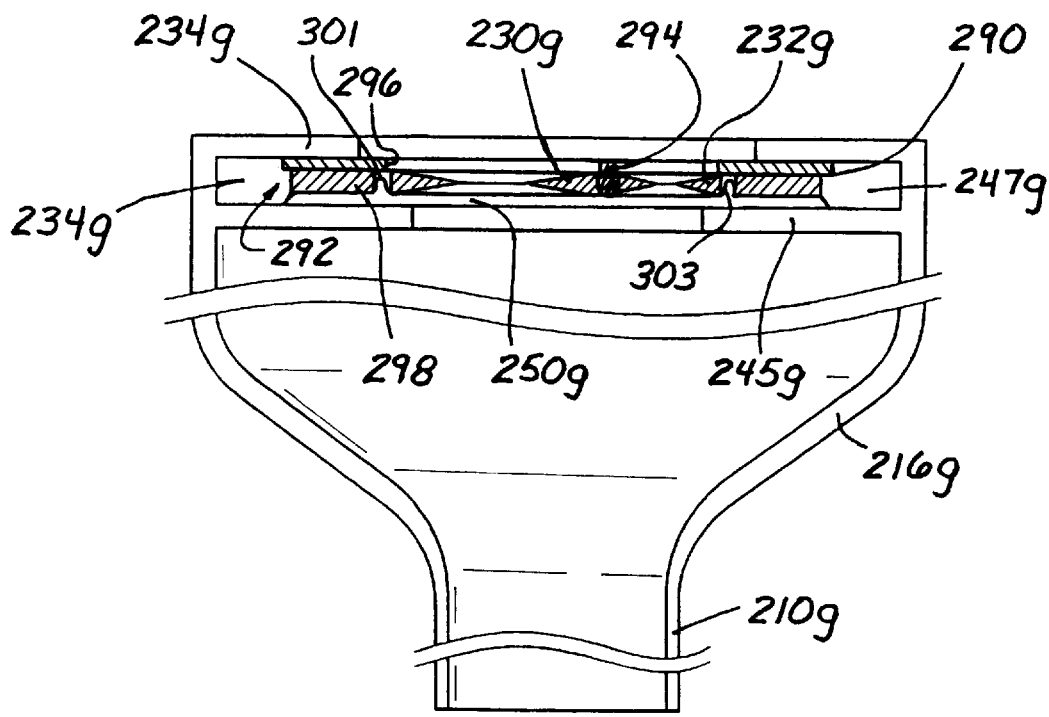
FIG. 32 is a cross-section view similar to FIG. 17 of a further embodiment having multiple flotation structures.

A further embodiment of the invention is illustrated in FIG. 32 wherein elements similar to those previously discussed are designated by the same reference numeral followed by the lower case letter "g". Thus, this embodiment includes the cannula 210g and the valve housing 216g, together with the end wall 243g and partition 245g which define the septum cavity 247g. In this case, the septum 234g floats within the cavity 247g and includes the septum valves 230g and 232g.

As previously noted, flotation of the septum 234g within the cavity 247g accommodates both valve selection and instrument manipulation. In the embodiment of FIG. 32, the second function, instrument manipulation, is further accommodated by a structure which floats the septum valves 230g and 232g within the septum 234g. As a result, flotation of the septum 234g within the cavity 247g primarily accommodates valve selection, while flotation of the septum valves 230g and 232g within the septum 234g primarily accommodates instrument manipulation.

In the illustrated embodiment, the septum 234g is formed with a rigid plate 290 that can be insert-molded to a resilient structure 292. The rigid plate 290 is provided with apertures 294 and 296, which provide access to the associated septum valves 232g and 230g. Both the rigid plate 290 and the resilient structure 292 have a generally planer configuration providing the septum 234g with a relatively low profile which is free to float within the cavity 247g.

The resilient structure 292 in this embodiment includes a perimeter block 298, which is fixed to the rigid plate 290 around the septum valves 230g and 232g. At least one accordion pleat 301 surrounds the septum valve 230g. A similar pleat 303 surrounds the septum valve 232g. These accordion pleats 301 and 303 provide the associated septum valves 230g and 232g with additional flotation characteristics which enable the valves to move relative to the other elements of the septum 234g. As a result, the septum valves 230g and 232g are free to float, not only with the septum 234g, but also within the septum 234g. By providing separate flotation structures, each structure can be varied to adjust the flotation characteristics of one type of flotation relative to the other type of flotation. For example, the accordion pleats 301 and 303 can provide a higher degree of flotation than that associated with the septum 234g moving within the cavity 247g. This insures that the septum valves 230g and 232g have a high degree of flotation accommodating even small degrees of instrument manipulation. This higher degree of flotation is particularly advantageous in avoiding the "cat eye effect" resulting from instrument manipulation. Flotation of the septum 234g within the cavity 247g is then primarily directed to septum selection which generally requires a higher degree of force to overcome friction associated with the cup seal 250g.

Figure 33:
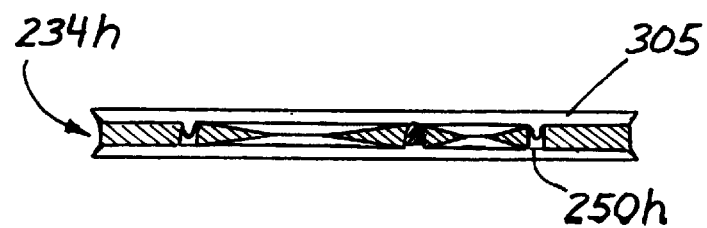
FIG. 33 is a cross-section view of a septum with multiple cup seals in still a further embodiment of the invention.

Another septum having these dual flotation characteristics is illustrated in FIG. 33 wherein elements similar to those previously discussed are designated by the same reference numeral followed by the lower case letter "h". In this case, the septum 234h is provided with the cup seal 250h, which floats in a sealing relationship with the inner surface of the partition 245g. However, in this embodiment, the rigid plate 290 of FIG. 32 is replaced by a second cup seal 305, which floats in a sealing relationship with the inner surface of the end wall 234g. The cup seals 250h and 305 can be formed integral with the perimeter block 298, but the second valves 230h and 232h remain free to float within the septum 234h.

With respect to all of the illustrated embodiments it should be noted that these are merely representative of many configurations which will now be apparent to those skilled in the art. The general concepts relating to a valve housing with a circular, elliptical, or polygonal configuration will now be appreciated. Other configurations for facilitating septum selection flotation in one or more directions, while inhibiting that flotation in another direction, will be of interest. Whether a single zero-closure valve is shared by multiple septum valves, or whether each septum valve is provided with its own zero-closure valve, can now be considered in various other combinations. Inhibiting leakage with cup seals, check valves, reciprocating valves, or any other valve combination can produce the advantages previously discussed. The skirts and valves disclosed to maintain air pressure within the trocar will give rise to other isolation structures of interest.

It is due to the wide variations which are possible with this invention that one is encouraged not to limit the concept to the embodiments illustrated and discussed, but rather to determine the scope of the invention only with reference to the following claims.

What is claimed is:

1. A surgical access device adapted to provide access for a surgical instrument across a body wall, comprising:

a cannula having a working channel extending between a proximal end and a distal end;

a valve housing disposed at the proximal end of the cannula;

a first valve disposed in the housing, the first valve having properties for being moved by operation of the instrument to slide within the housing between a first location and a second location for valve selection, and to float omni-directionally within the housing to form an instrument seal with the instrument and to maintain the instrument seal during manipulation of the instrument;

a second valve disposed in the housing with the first valve and having zero-closure characteristics; and portions of the housing defining a cavity sized and configured to receive at least the first valve in the floating relationship with the housing.

2. The surgical access device recited in claim 1, wherein:

the valve housing in radial cross-section has the general configuration of a rectangle having a long dimension and a short dimension; and the first valve has properties for sliding a first distance in a direction generally parallel to the long dimension of the rectangle to provide for selection of the first valve.

3. The surgical access device recited in claim 2, wherein:

the first valve has properties for floating a second distance in a second direction generally parallel to the short dimension of the rectangle; and the first distance is greater than the second distance.

4. The surgical access device recited in claim 3, wherein:

the first valve is slideable between a first position and a second position;

the first valve in the first position being generally aligned with the second valve; and the first valve in the second position being generally misaligned with the second valve.

5. The surgical access device recited in claim 4 wherein the first valve in the second position is blocked from communication with the working channel.

6. The surgical access device recited in claim 5 wherein the first valve in the second position is blocked by portions of the housing.

7. The surgical access device recited in claim 6 wherein the first valve includes at least one cup valve slideable along the housing portions and forming a seal with the housing portions to block the first valve in the second position of the first valve.

8. The surgical access device recited in claim 5 further comprising a check valve moveable with the first valve and having properties for blocking the first valve when the first valve is in the second position.

9. A surgical access device, comprising:

a cannula having an axis and extending between a proximal end and a distal end;

a valve housing disposed at the proximal end of the cannula;

a septum having properties for floating between a first position and a second position;

portions of the septum defining a first valve;

a second valve disposed in the valve housing and having zero-closure characteristics;

the first valve being generally aligned with the second valve when the septum is in the first position;

the first valve being generally misaligned with the second valve when the septum is in the second position; and a first check valve moveable with the septum and being oriented relative to the first valve, the first check valve having properties for blocking the first valve when the septum is in the second position.

10. The surgical access device recited in claim 9 wherein the portions of the septum are first portions, and the access device further comprises:

second portions of the septum defining a third valve;

the third valve being moveable with the first valve between the first position and the second position of the septum;

the third valve being generally aligned with the second valve when the septum is in the second position, and being generally misaligned with the second valve when the septum is in the first position; and a second check valve moveable with the septum and being first oriented relative to the third valve, the second check valve having properties for blocking, the third valve when the septum is in the first position.

11. The surgical access device recited in claim 10, wherein:

the first check valve and the second check valve form a reciprocating valve;

a first lever arm included in the reciprocating valve;

a second lever arm included in the reciprocating valve; and a first blocking member disposed on the first lever arm and having a diameter sufficient to block the first valve in the second position.

12. The surgical access device recited in claim 11 wherein the reciprocating valve further comprises:

a second blocking element disposed on the second lever and having properties for blocking the third valve when the septum is in the first position.

13. The surgical access device recited in claim 12 further comprising:

the first septum valve having a first diameter in a natural state;

the third valve having a second diameter in a natural state;

the first blocking member has a diameter greater than the first diameter of the first valve; and the second blocking member has a diameter greater than the second diameter of the third valve.

14. An access device, comprising:

a cannula having an axis extending between a proximal end and a distal end;

a valve housing disposed at the proximal end of the cannula and including portions defining a cavity having a generally planar configuration and extending transverse to the axis of the cannula;

a valve assembly disposed in the housing;

a septum valve included in the valve assembly;

a zero-closure valve included in the valve assembly and being generally aligned with the septum valve;

the septum valve being sized and configured to float within the cavity of the valve housing; and the zero-closure valve being coupled to the septum valve and having properties for floating with the septum valve relative to the housing.

15. The access device recited in claim 14, wherein:

the valve assembly has an axis which is generally parallel to the axis of the cannula; and the valve assembly floats between a first position wherein the axis of the valve assembly is generally parallel to and misaligned with the axis of the cannula, and in a second position wherein the axis of the valve assembly is generally parallel to and aligned with the axis of the cannula.

16. The access device recited in claim 15 wherein the portions of the housing define an opening and the zero-closure valve is coupled to the septum valve through the opening in a generally fixed relationship with the septum valve.

17. A surgical access assembly, comprising:
a cannula having an axis extending between a proximal end and a distal end;
a valve housing disposed at the proximal end of the cannula;
at least one septum valve disposed within the valve housing and having properties for floating within the housing between a first position wherein the septum valve is generally aligned with the axis, and a second position wherein the septum valve is generally misaligned with the axis; and
a blocking member having properties for blocking the septum valve in the second position.

18. The surgical access assembly recited in claim 17, further comprising:
a biasing element for supporting the blocking member and for biasing the blocking member to block the septum valve in the second position.

19. The surgical access assembly recited in claim 18 wherein the biasing element and the blocking member are integral and the biasing element is formed from an elastomeric material.

20. The surgical access assembly recited in claim 18 wherein the septum valve is a first septum valve and the blocking member is a first blocking member, the access assembly further comprising:
a second septum valve disposed within the valve housing and moveable with the first septum valve; and
a second blocking member having properties for blocking the second septum valve when the first septum valve is in the first position.

21. A surgical access assembly, comprising:
a cannula having an axis extending between a proximal end and a distal end;
a valve housing disposed at the proximal end of the cannula;
a septum valve assembly disposed in sealing engagement with the valve housing;
a first septum valve included in the septum valve assembly;
a second septum valve included in the septum valve assembly and having a spaced relationship with the first septum valve;
a first check valve included in the septum valve assembly and having properties for blocking the first septum valve; and
a second check valve included in the septum valve assembly and having properties for blocking the second septum valve.

22. The surgical access assembly recited in claim 21 wherein the septum valve assembly floats in sealing engagement with the valve housing between a first position and a second position.

23. The surgical access assembly recited in claim 22, wherein:
the septum valve assembly in the first position being characterized by the first septum valve in general alignment with the axis of the cannula;
the septum valve assembly in the second position being characterized by the first septum valve in general misalignment with the axis of the cannula; and
the first check valve having properties for blocking the first septum valve in the second position of the first septum valve.

24. The surgical access assembly recited in claim 23, further comprising:
the septum valve assembly in the first position being characterized by the second septum valve disposed in general misalignment with the axis of the cannula;
the septum valve assembly in the second position being characterized by the second septum valve disposed in general alignment with the axis of the cannula; and
the second check valve having properties for blocking the second septum valve in the first position of the septum valve assembly.

25. A surgical access device, comprising:
a cannula having an axis extending between a proximal end and a distal end;
a valve housing disposed at the proximal end of the cannula;
a septum disposed in the valve housing and having properties for floating relative to the valve housing;
first portions of the septum defining a perimeter block;
second portions of the septum defining at least one septum valve having properties for floating relative to the perimeter block of the septum.

26. The surgical access device recited in claim 25, wherein:
the housing includes a partition and an end wall which define a septum cavity; and
the perimeter block of the septum is free to float within the septum cavity to accommodate valve selection.

27. The surgical access device recited in claim 26, wherein the septum further comprises at least one cup seal having a floating and sealing relationship with an associated one of the partition and the end wall defining the septum cavity.

28. The surgical access device recited in claim 26, wherein the septum further comprises a rigid plate having a fixed relationship with the perimeter block of the septum.

29. A surgical access device, comprising:
a cannula having an axis extending between a proximal end and distal end;
a valve housing disposed at the proximal end of the cannula;
a septum disposed in the valve housing;
a septum valve disposed within the septum;
a first flotation structure having properties for floating the septum within the valve housing; and
a second flotation structure having properties for floating a septum valve within the septum.

30. The surgical access device recited in claim 29, further comprising:
a second septum valve included in the septum;
portions of the valve housing defining a septum cavity; and
the first flotation structure providing for movement of the septum within the septum cavity to facilitate selection of one of the first septum valve and second septum valve.

31. The surgical access device recited in claim 21 and being adapted for use with a surgical instrument, comprising:

a septum block included in the septum;

the second flotation structure included in the septum and disposed between the septum block and the septum valve to facilitate flotation of the septum valve relative to the septum block in response to manipulation of the surgical instrument.

32. A surgical access device, comprising:

a cannula extending between a proximal end and a distal end;

a seal housing coupled to the cannula at the proximal end of the cannula, the seal housing forming with the cannula a working channel;

a septum disposed in the seal housing and extending at least partially across the working channel; and a septum valve included in the septum and having properties for floating with the septum relative to the seal housing between a first position wherein the septum valve is aligned with the working channel and a second position wherein the septum valve is misaligned with the working channel.

33. The surgical access device recited in claim 32, further comprising:

means for blocking the septum valve in the second position.

34. The surgical access device recited in claim 33 wherein the blocking means includes portions of the seal housing that extend across the septum valve in the second position of the septum valve.

35. The surgical access device recited in claim 33 wherein the blocking means includes a check valve movable with the septum valve between the first position and the second position of the septum valve.

36. The surgical access device recited in claim 33 wherein the septum valve is a first septum valve and the device further comprises:

a second septum valve included in the septum and having properties for moving between a third position wherein the second septum valve is in alignment with the working channel and a fourth position wherein the second septum valve is misaligned with the working channel.

37. The surgical access device recited in claim 36 wherein the blocking means includes a reciprocating valve for alternatively blocking the first septum valve in the second position and the second septum valve in the fourth position.

38. The surgical access device recited in claim 32, further comprising:

a zero-closure valve coupled to the septum valve and movable with the septum valve between the first position and the second position.

39. The surgical access device recited in claim 36, further comprising:

a first zero-closure valve movable with the first septum valve between the first position and the second position; and a second zero-closure valve movable with the second septum valve between the third position and the fourth position.

* * * * *